US010260079B2

(12) United States Patent
Jiang et al.

(10) Patent No.: US 10,260,079 B2
(45) Date of Patent: *Apr. 16, 2019

(54) METHOD FOR PRODUCING ERGOTHIONEINE BY USING SOYBEAN CAKE POWDER AS NITROGEN SOURCE IN A SEED MEDIUM

(71) Applicants: TIANJIN INSTITUTE OF INDUSTRIAL BIOTECHNOLOGY, CHINESE ACADEMY OF SCIENCES, Tianjin (CN); TIANJIN SINONOCY BIOLOGICAL TECHNOLOGY CO., LTD., Tianjin (CN)

(72) Inventors: Wenxia Jiang, Tianjin (CN); Qi Liu, Tianjin (CN); Weiya Zhang, Tianjin (CN); Baoliang Mei, Tianjin (CN)

(73) Assignees: TIANJIN INSTITUTE OF INDUSTRIAL BIOTECHNOLOGY, CHINESE ACADEMY OF SCIENCES, Tianjin (CN); TIANJIN SINONOCY BIOLOGICAL TECHNOLOGY CO., LTD., Tianjin (CN)

(*) Notice: Subject to any disclaimer, the term of this patent is extended or adjusted under 35 U.S.C. 154(b) by 8 days.

This patent is subject to a terminal disclaimer.

(21) Appl. No.: 15/315,077

(22) PCT Filed: May 29, 2015

(86) PCT No.: PCT/CN2015/000372
§ 371 (c)(1),
(2) Date: Nov. 30, 2016

(87) PCT Pub. No.: WO2015/180492
PCT Pub. Date: Dec. 3, 2015

(65) Prior Publication Data
US 2017/0211107 A1 Jul. 27, 2017

(30) Foreign Application Priority Data
May 30, 2014 (CN) .......................... 2014 1 0243400

(51) Int. Cl.
*C12P 17/10* (2006.01)
*C12N 1/14* (2006.01)
*C12P 13/04* (2006.01)
*C12R 1/645* (2006.01)

(52) U.S. Cl.
CPC ............... *C12P 17/10* (2013.01); *C12N 1/14* (2013.01); *C12P 13/04* (2013.01); *C12N 2500/32* (2013.01); *C12N 2500/35* (2013.01); *C12R 1/645* (2013.01)

(58) Field of Classification Search
None
See application file for complete search history.

(56) References Cited

FOREIGN PATENT DOCUMENTS

| CN | 102978121 A | 3/2013 |
| CN | 103184246 A | 7/2013 |
| CN | 103734022 A | 4/2014 |

OTHER PUBLICATIONS

Huang et al. Sichuan Daxue Xuebao, Ziran Kexueban (2008), 45(3), 699-702 (abstract).*
Liu et al. Weishengwuxue Zazhi (2001), 21(2), 15-17 (abstract).*
Lee W Y et al., "Supplementation of Methionine Enhanced the Ergothioneine Accumulation in the Ganoderma Neo-Japonicum Mycelia", Appl Biochem Biotechnol 158:213-221 (2009).
Liang C-H et al., "Submerged Cultivation of Mycelium With High Ergothioneine Content from the Culinary-Medicinal King Oyster Mushroom *Pleurotus eryngii* (Higher Basidiomycetes) and its Composition", International Journal of Medicinal Mushrooms 15(2):153-164 (2013).
Liu Q. et al., "Research Progress on the Biosynthesis Technology of L-Ergothioneine", Symposium of International Summit Forum on Amino Acid Industry Development in 2013, pp. 22-27 (2013), together with an English-language abstract.
Liu Q. et al., "L-Ergothioneine—A Multifunctional Physiological Cytoprotector", Nat Prod Res Dev 25:160-164, 85 (2013), together with an English-language abstract.
Tepwong P. et al., "Mycobial Enhancement of Ergothioneine by Submerged Cultivation of Edible Mushroom Mycelia and its Application as an Antioxidative Compound", Food Chemistry 131:247-258 (2012).
Written Opinion of the International Searching Authority dated Aug. 24, 2015 received in International Application No. PCT/CN2015/000372.
International Search Report dated Aug. 24, 2015 issued in PCT/CN2015/000372.

(Continued)

*Primary Examiner* — Christian L Fronda
(74) *Attorney, Agent, or Firm* — Scully Scott Murphy & Presser

(57) ABSTRACT

The present disclosure relates to an improved method for producing ergothioneine, comprising the steps of: (a) inoculating *Pleurotus ostreatus* strain CGMCC No.6232 into a seed medium, and culturing it to prepare a seed liquor, wherein the seed medium uses soybean cake powder as nitrogen source; and (b) inoculating the seed liquor into a fermentation basal medium, and then culturing it to obtain a fermentation broth of *Pleurotus ostreatus* mycelia. Further, any one or more members selected from $NH_4Cl$, $NH_4NO_3$, NaCl, polyethylene glycol, folic acid, vitamin B1 (VB1), indolebutyric acid, citric acid, pyruvic acid, arginine, lysine, leucine, aspartic acid, glutamic acid, betaine, histidine, cysteine, methionine, tween, span, chitosan, Fluconazole, Miconazole, Ketoconazole, ethylenediaminetetraacetic acid (EDTA), isopropyl alcohol and dimethyl sulfoxide are added into the fermentation basal medium.

15 Claims, No Drawings

(56) References Cited

OTHER PUBLICATIONS

Database WPI, Week 201457; Thompson Scientific, London, GB, AN 2014-L55165 dated Apr. 23, 2014, Abstract Only, 2 pages.
Database WPI, Week 201381; Thompson Scientific, London, GB, AN 2013-T00754 dated Jul. 3, 2013, Abstract Only, 2 pages.
Database WPI, Week 201359; Thompson Scientific, London, GB, AN 2013-K63184 dated Mar. 20, 2013, Abstract Only, 2 pages.
Tepwong, P. et al., "Mycobial enhancement of ergothioneine by submerged cultivation of edible mushroom mycelia and its application as an antioxidative compound", Food Chemistry, Aug. 25, 2011, vol. 131, No. 1, pp. 247-258.
Then, S. et al., "Contents of Iovastatin, Y-aminobutyric acid and ergothioneine in mushroom fruiting bodies and mycelia", Food Science and Technology, Jan. 17, 2012, vol. 47, No. 2, pp. 274-278.
Bao-Liang, M. et al., "Study on the Biosynthesis of L-ergothioneine by Enhancement of Nutritional Factors", Food Research and Development, Sep. 9, 2015, vol. 36, No. 15, pp. 108-112, with English Abstract.
Extended European Search Report dated Dec. 15, 2017 issued in European Patent Application No. 15798883.3.

\* cited by examiner

US 10,260,079 B2

METHOD FOR PRODUCING ERGOTHIONEINE BY USING SOYBEAN CAKE POWDER AS NITROGEN SOURCE IN A SEED MEDIUM

TECHNICAL FIELD

The present disclosure belongs to the field of biological resources, biological engineering, fermentation engineering and biosynthesis of natural products. More specifically, the present disclosure relates to a method for producing ergothioneine with a higher yield.

BACKGROUND ART

Ergothioneine (EGT) is a rare natural chiral amino acid, and as an important physiologically active substance in the living body, ergothioneine has many biological functions such as antioxidation, preventing ultraviolet radiation damages, regulating oxidation-reduction reactions in the cells, chelating divalent metal ions, participating in energy regulation in the cells and so on, and thus ergothioneine is a multifunctional cellular physiological protector (Qi Liu, Wen-xia Jiang, Ping Yang, Tao Zhou, L-Ergothioneine—A multifunctional physiological cytoprotector [J]. *Nat. Pro. Res. Dev.,* 2013, 25 (Suppl.): 160-164.). Ergothioneine is a product generally recognized as safe (GRAS) with stable property, which has important application values and broad application prospects in the industries of pharmaceuticals, biomedicine, food, health food, food additives, cosmetics, etc.

Since the production cost of ergothioneine is high at present, the application thereof is limited. As compared with a chemical synthesis method and a natural biological extraction method, producing ergothioneine by submerged fermentation of edible fungus may improve the accumulation of ergothioneine, achieve large-scale efficient production, reduce production costs, and have the advantages of product safety, etc. by establishing a control strategy for a high density fermentation process, and thus is the development direction of synthetizing ergothioneine (Qi Liu, Wei-ya Zhang, Wen-xia Jiang, Bao-liang Mei, Tao Zhou, Research progress of ergothioneine biosynthesis technology [C]. *Symposium of international summit forum on amino acid industry development in 2013.* 2013: 22-27.).

Pramvadee Tepwong et al. in Japan produced ergothioneine by submerged fermentation of *Lentinula edodes* mycelia, and the yield of ergothioneine was 23.6 mg/L in the fermentation broth after fifteen days fermentation. (Pramvadee Tepwong, Anupam Giri, Fumito Sasaki. Microbial enhancement of ergothioneine by submerged cultivation of edible mushroom mycelia and its application as an antioxidative compound [J]. *Food Chemistry,* 2012, 131: 247-258.); Wi Young Lee et al. in Korea synthesized ergothioneine by fermentation of *Ganoderma neo-japonicum* mycelia, and the content of ergothioneine in the fermentation broth reached 57.5 mg/L at the end of fermentation (Wi Young Lee, Eung-Jun Park, Jin Kwon Ahn. Supplementation of methionine enhanced the ergothioneine accumulation in the *Ganoderma neo-japonicum* mycelia [J]. *Appl Biochem Biotechnol,* 2009, 158: 213-221.); Ling-yi Huang and Chih-hung Liang in Taiwan subjected *Pleurotus eryngii* mycelia to liquid fermentation and culture, and after the culture, the yield of ergothioneine in the fermentation broth reached 62.2 mg/L (Ling-yi Huang. Submerged cultivation and physiological activities of *Pleurotus eryngii* mycelia with a high ergothioneine content [D]. *Taiwan: National Chung Hsing University,* 2010) and 60.4 mg/L (Chih-Hung Liang, Ling-Yi Huang, Kung-Jui Ho, et al. Submerged cultivation of mycelium with high ergothioneine content from the culinary-medicinal king oyster mushroom *Pleurotus eryngii* (higher basidiomycetes) and its composition [J]. *International Journal of Medicinal Mushrooms,* 2013, 15(2): 153-164.), respectively; Wen-xia Jiang et al. produced ergothioneine by fermentation of *Pleurotus ostreatus* mycelia, and through the optimization of fermentation medium and fermentation control process, the content of ergothioneine in the fermentation broth reached 135.7 mg/L (Wen-xia Jiang, Qi Liu, Tao Zhou. The strain for producing ergothioneine and method for producing ergothioneine [P]. CN 201210392417.8).

SUMMARY

The object of the present disclosure is to further improve the fermentation yield of ergothioneine in Chinese Patent Invention Application CN 201210392417.8, and to provide an modified method for producing ergothioneine. The entire contents of Chinese patent invention application CN 201210392417.8 are incorporated herein by reference.

In Chinese patent invention application CN 201210392417.8, disclosed is a method for producing ergothioneine, comprising the steps of:

1) inoculating *Pleurotus ostreatus* strain CGMCC No. 6232 (preferably strains from the PDA slant) into a liquid seed medium, culturing it on a shaker at 100-200 rpm at 19-31° C. for at least 3 days to prepare a seed liquor;

2) inoculating the seed liquor into a fermentation medium with an inoculation amount of 4-20% (V/V), and then culturing it on a shaker at 100-200 rpm at 19-31° C. for at least 6 days to obtain a fermentation broth of *Pleurotus ostreatus* mycelia;

3) heating the fermentation broth of the mycelia to 50-100° C. after the fermentation, stirring for extraction at 0-600 rpm for 10-100 min, thereby extracting ergothioneine from the mycelial cells to the fermentation broth outside the cells.

The liquid seed medium is consisting of: corn flour 15-50 g/L (preferably 25-40 g/L), soybean meal powder 10-35 g/L (preferably 15-25 g/L), α-amylase 20-80 U/L (preferably 30-65 U/L), $KH_2PO_4$ 1-6 g/L (preferably 2-4.5 g/L), $MgSO_4 \cdot 7H_2O$ 0.2-5 g/L (preferably 0.2-3 g/L), and a balance of water.

The fermentation medium is consisting of: glycerol 10-80 g/L, casein peptone 10-40 g/L, $KH_2PO_4$ 2-4 g/L, $MgSO_4 \cdot 7H_2O$ 0.5-2 g/L, and a balance of water.

The Technical Solution of the Present Disclosure

According to the present disclosure, *Pleurotus ostreatus* TIB.BPE.10010 was used as a fermentation strain for producing ergothioneine by fermentation. The strain was deposited in China General Microbiological Culture Collection Center (CGMCC) on Jun. 15, 2012 with the accession number being CGMCC No. 6232.

The production method for further improving the fermentation yield of ergothioneine according to the present disclosure comprises the steps of:

(a) inoculating *Pleurotus ostreatus* strain CGMCC No.6232 into a seed medium, and culturing it to prepare a seed liquor, wherein the seed medium uses soybean cake powder as nitrogen source; and (b) inoculating the seed liquor into a fermentation basal medium, and then culturing it to obtain a fermentation broth of *Pleurotus ostreatus* mycelia.

Preferably, *Pleurotus ostreatus* CGMCC No. 6232 is obtained from a PDA slant medium; the seed medium is consisting of: corn flour 15-50 g/L (preferably 25-40 g/L), soybean cake powder 5-35 g/L (preferably 15-35 g/L), α-amylase 20-80 U/L (preferably 30-80 U/L), $KH_2PO_4$ 1-6 g/L (preferably 2-4.5 g/L), $MgSO_4 \cdot 7H_2O$ 0.2-5 g/L (preferably 0.2-3 g/L), and a balance of water; the fermentation basal medium is consisting of: glycerol 10-95 g/L (preferably 65-95 g/L), casein peptone 10-80 g/L (preferably 40-80 g/L), $KH_2PO_4$ 2-4 g/L, $MgSO_4 \cdot 7H_2O$ 0.5-2 g/L, and a balance of water.

Preferably, the culturing process in step (a) is carried out at 19-31° C. for at least 3 days, the culturing process in step (b) is carried out at 19-31° C. for at least 6 days, and the inoculation amount in step (b) is 4-20% (V/V).

Further, any one or more members selected from $NH_4Cl$, $NH_4NO_3$, NaCl, polyethylene glycol, folic acid, vitamin B1 (VB1), indolebutyric acid, citric acid, pyruvic acid, arginine, lysine, leucine, aspartic acid, glutamic acid, betaine, histidine, cysteine, methionine, tween (for example, tween 60 and tween 80), span (for example, span 80), chitosan, Fluconazole, Miconazole, Ketoconazole, ethylenediaminetetraacetic acid (EDTA), isopropyl alcohol and dimethyl sulfoxide are added into the fermentation basal medium, and the adding step may be carried out before the fermentation or during the fermentation.

Preferably, any one or more members selected from $NH_4Cl$ 0.5 g/L-12 g/L, $NH_4NO_3$ 0.5 g/L-10 g/L, NaCl 0.5 g/L-20 g/L, polyethylene glycol (for example, PEG 6000) 0.2 g/L-5 g/L, folic acid 0.08 g/L-2.56 g/L, VB1 0.01 g/L-0.8 g/L, indolebutyric acid 0.1 mg/L-4 mg/L, citric acid 0.01 g/L-0.8 g/L, pyruvic acid 0.05 g/L-4.5 g/L, arginine 0.1 g/L-7 g/L, lysine 0.1 g/L-8 g/L, leucine 0.02 g/L-0.5 g/L, aspartic acid 0.05 g/L-9 g/L, glutamic acid 1 μmol/L-100 μmol/L, betaine 50 mmol/L-250 mmol/L, histidine 0.1 mmol/L-3 mmol/L, cysteine 2 mmol/L-45 mmol/L, methionine 3 mmol/L-45 mmol/L, tween 0.5 g/L-50 g/L (for example, tween 60 2 g/L-50 g/L, tween 80 0.5 g/L-40 g/L), span 0.2 g/L-10 g/L (for example, span 80 0.2 g/L-10 g/L), chitosan 0.2 g/L-0.4 g/L, Fluconazole 2 mg/L-80 mg/L, Miconazole 0.5 mg/L-50 mg/L, Ketoconazole 0.5 mg/L-50 mg/L, ethylenediaminetetraacetic acid (EDTA) 0.05 g/L-0.5 g/L, isopropyl alcohol 0.5%-2% (V/V) and dimethyl sulfoxide 0.5%-2% (V/V) in specified amounts are added into the fermentation basal medium.

Further, the temperature of fermentation is preferably adjusted to 25-31° C. in the process of fermentation in step (b). For example, the temperature is controlled to 25° C. at the beginning of fermentation, and the temperature is controlled to 28-31° C. on the fourth day and is maintained to the end of fermentation.

Further, the pH of the fermentation broth is preferably adjusted to 4.8-6.3 in the process of fermentation in step (b). For example, the pH is controlled to 5.0-6.3 on the fourth day of the fermentation and is maintained to the end of fermentation.

Further, preferably the pressure is adjusted to 0.05-0.1 Mpa and the dissolved oxygen is adjusted to 15-30% in the process of fermentation in step (b).

In one embodiment, a method for producing ergothioneine in the present disclosure comprises the steps of: (a) inoculating *Pleurotus ostreatus* strain CGMCC No.6232 into a seed medium, and culturing it at 25-28° C. for 3-5 days to prepare a seed liquor, the seed medium comprising 25-40 g/L corn flour, 15-35 g/L soybean cake powder, 30-80 U/L α-amylase, 2-4.5 g/L $KH_2PO_4$, 0.2-3 g/L $MgSO_4 \cdot 7H_2O$, and a balance of water; and (b) inoculating the seed liquor into a fermentation basal medium with an inoculation amount of 4-20% (V/V), and culturing it at 25-31° C. for at least 6 days to obtain a fermentation broth of *Pleurotus ostreatus* mycelia, the fermentation basal medium comprising 65-95 g/L glycerol, 40-80 g/L casein peptone, 2-4 g/L $KH_2PO_4$, 0.5-2 g/L $MgSO_4 \cdot 7H_2O$, 7.5-15 mmol/L methionine, 7.5-15 mmol/L cysteine, and a balance of water.

The Technical Effect of the Present Disclosure

The fermentation level of ergothioneine can be significantly improved and the yield of the product may be significantly higher than that of the control group by using soybean cake powder as nitrogen source of the seed medium for fermentation of *Pleurotus ostreatus* CGMCC No. 6232 to synthesize ergothioneine, properly increasing the amount of glycerol and casein peptone in the fermentation medium, adding any one or more compounds selected from $NH_4Cl$, $NH_4NO_3$, NaCl, polyethylene glycol, folic acid, vitamin B1 (VB1), indolebutyric acid, citric acid, pyruvic acid, arginine, lysine, leucine, aspartic acid, glutamic acid, betaine, histidine, cysteine, methionine, tween, span, chitosan, Fluconazole, Miconazole, Ketoconazole, ethylenediaminetetraacetic acid (EDTA), isopropyl alcohol and dimethyl sulfoxide into the fermentation basal medium, adjusting the temperature of fermentation in the process of fermentation, adjusting the pH of the fermentation broth in the process of fermentation, and/or adjusting the pressure and the dissolved oxygen in the process of fermentation. In particular, the amount of extracellular ergothioneine in the fermentation broth may be also improved by adding any one or more compounds selected from tween, Fluconazole, Miconazole, Ketoconazole, ethylenediaminetetraacetic acid (EDTA), isopropyl alcohol and dimethyl sulfoxide into the fermentation basal medium.

DETAILED DESCRIPTION

The following examples of the present disclosure are only used to illustrate the particular embodiments for implementation of the present disclosure, and those particular embodiments cannot be understood to limit the present disclosure.

Any other changes, modifications, substitutions, combinations, or simplifications without departing from the sprit and principles of the present disclosure are regarded as equivalents that fall within the protection scope of the present disclosure.

Experimental instruments and materials: Shaker (IS-RDV3, Crystal Technology & Industries, Inc.); 75 L automatic control fermentor (BIO-DDCU type, Sartorius Stedim Biotech Co., Ltd.); HPLC (Agilent 1260, Agilent Technologies); Water-bath (TW20, Julabo Company); Digital heating magnetic agitator (MIX Control 20, WIGGENS Company); Electronic analytical balance (AB204-S, METTLER TOLEDO); Piston vacuum pump (V610, ChemVak); Ultrasonic wave cleaner (SB-5200D type, NingBo Scientz Biotechnology Co., Ltd.); 0.22 μm Millipore filter (Tianjin Bonna-Agela Technologies Inc.); Hollow fiber ultrafiltration membrane (Tianjin Aisheng Membrane Filtration Technology Co., Ltd.).

Main reagents: reference L-ergothioneine (purity≥98%, Biomol International Inc.); PDA medium (Becton, Dickinson and Company); Methanol and the like reagents are of the commercially available chromatographic purity; $KH_2PO_4$, $MgSO_4.7H_2O$, and citric acid are purchased from Sinopharm Chemical Reagent Co., Ltd.; Corn flour is purchased from Meihekou Xingda rice industry Co., Ltd.; Soybean cake powder and soybean meal powder are purchased from Beijing Zhongmian Ziguang Biological Technology Co., Ltd.; Glycerol is purchased from Tianjin Fengchuan Chemical Reagent Technologies Co., Ltd.; Casein peptone is purchased from Yanshi Baijia industry & trade Co., Ltd.; $NH_4Cl$, $NH_4NO_3$, NaCl, polyethylene glycol, pyruvic acid and span 80 are purchased from Tianjin Guangfu Fine Chemical Co., Ltd.; α-amylase, folic acid, VB1, indolebutyric acid, arginine, lysine, leucine, glutamic acid, aspartic acid, histidine, cysteine, methionine, chitosan, Fluconazole, Miconazole and Ketoconazole are purchased from Beijing Solarbio Technology Co., Ltd.; Betaine is a product from Weifang Xiangweisi Chemicals Co., Ltd.; Tween 60 and tween 80 are purchased from Beijing Solarbio Technology Co., Ltd.; EDTA is purchased from Chengdu Geleixiya Chemical Technology Co., Ltd.; Isopropyl alcohol is purchased from Tianjin Bonna-Agela Technologies Inc.; Dimethyl sulfoxide is purchased from Tianjin Guangfu Fine Chemical Research Institute.

Comparative Example 1: Preparation of a Fermentation Broth of Mycelia Containing Ergothioneine and Detection of Ergothioneine Preparation of a Fermentation Broth of Mycelia Containing Ergothioneine Seed medium: corn flour 30 g/L, soybean meal powder 15 g/L, α-amylase 80 U/L, $KH_2PO_4$ 3 g/L, $MgSO_4.7H_2O$ 1.5 g/L, and a balance of water. The seed medium was sterilized at 121° C. for 20 min, and the liquid volume in a 500 mL triangular flask was 150 mL.

Fermentation basal medium: glycerol 50 g/L, casein peptone 35 g/L, $KH_2PO_4$ 3 g/L, $MgSO_4.7H_2O$ 1.5 g/L, and a balance of water. The fermentation basal medium was sterilized at 121° C. for 20 min, and the liquid volume in a 500 mL triangular flask was 150 mL.

A lawn of the strain CGMCC No. 6232 was picked from the PDA slant and inoculated into the seed medium, cultured on a shaker at 150 rpm at 25° C. for 4 days, to obtain a seed liquor. The seed liquor was inoculated into the fermentation basal medium with an inoculation amount of 5% in volume ratio, cultured on a shaker at 150 rpm at 25° C. for 15 days, thereby obtaining a fermentation broth of the mycelia, wherein a majority of ergothioneine was accumulated in mycelial cells.

The content of ergothioneine in the fermentation broth prepared as such was 110.8 mg/L, and the determination method is as described below.

Preparation of a Test Sample for Detection of the Content of Extracellular Ergothioneine in the Filtrate After submerged fermentation of *Pleurotus ostreatus* mycelia CGMCC No. 6232, 20 mL of the fermentation broth of the mycelia was filtered with a white cloth, and the filtrate was collected and then filtered using an ultrafiltration membrane with a molecular weight cut off (MWCO) of 4 kDa. The obtained permeate was the test sample for detection of the content of extracellular ergothioneine in the filtrate.

Preparation of a Test Sample for Detection of the Total Content of Ergothioneine in the Fermentation Broth The fermentation broth of the mycelia was placed in a water bath at 90° C., stirred for extraction at 200 rpm for 15 min, thereby extracting ergothioneine to the outside of cells. The resultant product was filtered, and the filtrate was collected and then filtered using an ultrafiltration membrane with MWCO of 4 kDa. The obtained permeate was the test sample for detection of the total content of ergothioneine in the fermentation broth.

Detection of Ergothioneine

Preparation of reference solutions: 10 mg of L-ergothioneine reference was accurately weighed, and was formulated in a 25 mL volumetric flask with purified water into a reference stock solution with a concentration of 400 mg/L. Then proper amounts of the stock solution were taken to form solutions with concentrations of 40 mg/L, 80 mg/L, 120 mg/L, 160 mg/L and 200 mg/L, respectively together with purified water. The solutions were filtered with 0.22 μm millipore filter to obtain the reference solutions. Qualitative and quantitative detection: L-ergothioneine reference solutions and the test samples were detected by HPLC under the same chromatographic conditions. The chromatograms of the test samples were compared with those of the L-ergothioneine reference solutions, and the chromatographic peak of L-ergothioneine in the test sample was identified based on the retention time. A standard curve was plotted with the concentrations of L-ergothioneine reference solutions and the corresponding peak areas. In the case that the sample load of the reference solution was identical with that of the test sample, an external standard method was used for quantification so as to calculate the content of ergothioneine in the test sample. The concentration of ergothioneine in the test sample was the concentration of ergothioneine in the fermentation broth.

Detection conditions: the chromatographic column was Agilent Eclipse XDB-C18 (4.6×250 mm, 5 μm), with two chromatographic columns in series; the mobile phase was 1% methanol solution, the pH of which was adjusted to 5.0 using acetic acid-sodium acetate buffer; the detection wavelength was 257 nm; the flow rate was 0.7 mL/min; the column temperature was 25° C.; and the sample load was 5 μL.

Example 1: Effect of Nitrogen Source of Seed Medium and Content Thereof on Ergothioneine Accumulation by Fermentation The fermentation broths were prepared according to the same method as in Comparative Example 1, except for using soybean cake powder of 5 g/L, 10 g/L, 15 g/L, 20 g/L, 25 g/L, 30 g/L, and 35 g/L, respectively instead of soybean meal powder with the same concentrations as nitrogen source of the seed mediums. *Pleurotus ostreatus* mycelia CGMCC No. 6232 were subjected to fermentation and culture. After the fermentation, the contents of ergothioneine in the fermentation broths were determined, and the results were shown in Table 1 and Table 2.

By using soybean cake powder instead of soybean meal powder with the same concentration as nitrogen source of the seed mediums, the contents of ergothioneine in the fermentation broths were all improved, among which, the average content of ergothioneine in the fermentation broth in the test group of soybean cake powder of 15 g/L reached 125.5 mg/L, which was improved by 13.3% compared with that in Comparative Example 1 (110.8 mg/L). In addition, the contents of extracellular ergothioneine in the filtrates were also determined, among which, the highest one was 7.14 mg/L.

Example 2: Addition of NH$_4$Cl Improves Ergothioneine Accumulation by Fermentation The fermentation broths were prepared with soybean cake powder of 15 g/L as nitrogen source of the seed medium according to the same method as in Example 1, except for additionally adding NH$_4$Cl of 0.5 g/L, 1 g/L, 2 g/L, 4 g/L, 8 g/L, and 12 g/L into the fermentation basal mediums, respectively, while the fermentation basal medium without NH$_4$Cl was used as a control group. *Pleurotus ostreatus* mycelia CGMCC No. 6232 were subjected to fermentation and culture. After the fermentation, the contents of ergothioneine in the fermentation broths were determined, and the results were shown in Table 3.

The experimental results showed that when the amounts of added NH$_4$Cl were in the range of 0.5 g/L-12 g/L, the contents of ergothioneine in the fermentation broths were all higher than that in the control group, among which, when the amount of added NH$_4$Cl was 4 g/L, the content of ergothioneine was the highest and reached 155.4 mg/L, which was improved by 24.4% compared with that in the control group.

TABLE 1

Effect of content of soybean cake powder in seed medium on ergothioneine accumulation by fermentation

| Content of soybean cake powder in seed medium (g/L) | 5 | 10 | 15 | 20 | 25 | 30 | 35 |
|---|---|---|---|---|---|---|---|
| Content of ergothioneine in fermentation broth (mg/L) | 84.2 ± 3.45 | 102 ± 1.53 | 125.5 ± 1.88 | 124.1 ± 2.26 | 119.6 ± 3.07 | 120.3 ± 2.89 | 112.5 ± 2.4 |

TABLE 2

Effect of content of soybean meal powder in seed medium on ergothioneine accumulation by fermentation

| Content of soybean meal powder in seed medium (g/L) | 5 | 10 | 15 | 20 | 25 | 30 | 35 |
|---|---|---|---|---|---|---|---|
| Content of ergothioneine in fermentation broth (mg/L) | 73.4 ± 1.66 | 91.3 ± 2.94 | 110.8 ± 2.12 | 108.6 ± 3.78 | 105.3 ± 2.57 | 106.7 ± 1.79 | 100.9 ± 2.42 |

TABLE 3

| Effect of amount of added NH$_4$Cl on ergothioneine accumulation by fermentation | | | | | | | |
|---|---|---|---|---|---|---|---|
| Amount of added NH$_4$Cl in fermentation medium (g/L) | 0 (control group) | 0.5 | 1 | 2 | 4 | 8 | 12 |
| Content of ergothioneine in fermentation broth (mg/L) | 124.9 ± 2.12 | 127 ± 1.87 | 133.7 ± 1.04 | 139.2 ± 1.55 | 155.4 ± 2.68 | 141.8 ± 0.68 | 128.6 ± 3.53 |

Example 3: Addition of NH$_4$NO$_3$ Improves Ergothioneine Accumulation by Fermentation The fermentation broths were prepared with soybean cake powder of 15 g/L as nitrogen source of the seed medium according to the same method as in Example 1, except for additionally adding NH$_4$NO$_3$ of 0.5 g/L, 1 g/L, 2.5 g/L, 5 g/L, 7.5 g/L, and 10 g/L into the fermentation basal mediums, respectively, while the fermentation basal medium without NH$_4$NO$_3$ was used as a control group. *Pleurotus ostreatus* mycelia CGMCC No. 6232 were subjected to fermentation and culture. After the fermentation, the contents of ergothioneine in the fermentation broths were determined, and the results were shown in Table 4.

The experimental results showed that when the amounts of added NH$_4$NO$_3$ were in the range of 0.5 g/L-10 g/L, the contents of ergothioneine in the fermentation broths were all higher than that in the control group, among which, when the amount of added NH$_4$NO$_3$ was 5 g/L, the content of ergothioneine was the highest and reached 148 mg/L, which was improved by 18.5% compared with that in the control group.

according to the same method as in Example 1, except for additionally adding NaCl of 0.5 g/L, 2 g/L, 5 g/L, 10 g/L, and 20 g/L into the fermentation basal mediums, respectively, while the fermentation basal medium without NaCl was used as a control group. *Pleurotus ostreatus* mycelia CGMCC No. 6232 were subjected to fermentation and culture. After the fermentation, the contents of ergothioneine in the fermentation broths were determined, and the results were shown in Table 5.

The experimental results showed that when the amounts of added NaCl were in the range of 0.5 g/L-20 g/L, the contents of ergothioneine in the fermentation broths were all higher than that in the control group, among which, when the amount of added NaCl was 5 g/L, the content of ergothioneine was the highest and reached 123.9 mg/L, which was improved by 6.63% compared with that in the control group.

TABLE 4

| Effect of amount of added NH$_4$NO$_3$ on ergothioneine accumulation by fermentation | | | | | | | |
|---|---|---|---|---|---|---|---|
| Amount of added NH$_4$NO$_3$ in fermentation medium (g/L) | 0 (control group) | 0.5 | 1 | 2.5 | 5 | 7.5 | 10 |
| Content of ergothioneine in fermentation broth (mg/L) | 124.9 ± 2.12 | 127.2 ± 1.18 | 134 ± 2.46 | 140.7 ± 3.74 | 148 ± 0.82 | 141.4 ± 1.98 | 129.7 ± 1.03 |

Example 4: Addition of NaCl Improves Ergothioneine Accumulation by Fermentation The fermentation broths were prepared with soybean cake powder of 15 g/L as nitrogen source of the seed medium

TABLE 5

Effect of amount of added NaCl on ergothioneine accumulation by fermentation

| Amount of added NaCl in fermentation medium (g/L) | 0 (control group) | 0.5 | 2 | 5 | 10 | 20 |
|---|---|---|---|---|---|---|
| Content of ergothioneine in fermentation broth (mg/L) | 116.2 ± 1.96 | 120.1 ± 0.76 | 121.7 ± 2.85 | 123.9 ± 1.85 | 122.7 ± 1.06 | 119.7 ± 1.2 |

Example 5: Addition of Polyethylene Glycol PEG 6000 Improves Ergothioneine Accumulation by Fermentation The fermentation broths were prepared with soybean cake powder of 15 g/L as nitrogen source of the seed medium according to the same method as in Example 1, except for additionally adding PEG 6000 of 0.2 g/L, 0.5 g/L, 1 g/L, 3 g/L, and 5 g/L into the fermentation basal mediums, respectively, while the fermentation basal medium without PEG 6000 was used as a control group. *Pleurotus ostreatus* mycelia CGMCC No. 6232 were subjected to fermentation and culture. After the fermentation, the contents of ergothioneine in the fermentation broths were determined, and the results were shown in Table 6.

The experimental results showed that when the amounts of added PEG 6000 were in the range of 0.2 g/L-5 g/L, the contents of ergothioneine in the fermentation broths were all higher than that in the control group, among which, when the amount of added PEG 6000 was 1 g/L, the content of ergothioneine was the highest and reached 124.4 mg/L, which was improved by 7.06% compared with that in the control group.

according to the same method as in Example 1, except for additionally adding folic acid of 0.08 g/L, 0.16 g/L, 0.32 g/L, 0.64 g/L, 1.28 g/L, and 2.56 g/L into the fermentation basal mediums, respectively, while the fermentation basal medium without folic acid was used as a control group. *Pleurotus ostreatus* mycelia CGMCC No. 6232 were subjected to fermentation and culture. After the fermentation, the contents of ergothioneine in the fermentation broths were determined, and the results were shown in Table 7.

The experimental results showed that when the amounts of added folic acid were in the range of 0.08 g/L-2.56 g/L, the contents of ergothioneine in the fermentation broths were all higher than that in the control group, among which, when the amount of added folic acid was 0.64 g/L, the content of ergothioneine was the highest and reached 148.6 mg/L, which was improved by 25% compared with that in the control group.

TABLE 6

Effect of amount of added PEG 6000 on ergothioneine accumulation by fermentation

| Amount of added PEG 6000 in fermentation medium (g/L) | 0 (control group) | 0.2 | 0.5 | 1 | 3 | 5 |
|---|---|---|---|---|---|---|
| Content of ergothioneine in fermentation broth (mg/L) | 116.2 ± 1.96 | 120.8 ± 2.28 | 121.3 ± 2.66 | 124.4 ± 1.35 | 123.1 ± 1.98 | 120.0 ± 2.69 |

Example 6: Addition of Folic Acid Improves Ergothioneine Accumulation by Fermentation The fermentation broths were prepared with soybean cake powder of 15 g/L as nitrogen source of the seed medium

TABLE 7

Effect of amount of added folic acid on ergothioneine accumulation by fermentation

| Amount of added folic acid in fermentation medium (g/L) | 0 (control group) | 0.08 | 0.16 | 0.32 | 0.64 | 1.28 | 2.56 |
|---|---|---|---|---|---|---|---|
| Content of ergothioneine in fermentation broth (mg/L) | 118.9 ± 2.37 | 121.4 ± 1.36 | 127.1 ± 2.24 | 136.9 ± 4.14 | 148.6 ± 1.54 | 143.8 ± 1.77 | 122.2 ± 3.03 |

TABLE 7-continued

Effect of amount of added folic acid on ergothioneine accumulation by fermentation

Example 7: Addition of VB1 Improves Ergothioneine Accumulation by Fermentation The fermentation broths were prepared with soybean cake powder of 15 g/L as nitrogen source of the seed medium according to the same method as in Example 1, except for additionally adding VB1 of 0.01 g/L, 0.05 g/L, 0.1 g/L, 0.2 g/L, 0.4 g/L, and 0.8 g/L into the fermentation basal mediums, respectively, while the fermentation basal medium without VB1 was used as a control group. *Pleurotus ostreatus* mycelia CGMCC No. 6232 were subjected to fermentation and culture. After the fermentation, the contents of ergothioneine in the fermentation broths were determined, and the results were shown in Table 8.

The experimental results showed that when the amounts of added VB1 were in the range of 0.01 g/L-0.8 g/L, the contents of ergothioneine in the fermentation broths were all higher than that in the control group, among which, when the amount of added VB1 was 0.1 g/L, the content of ergothioneine was the highest and reached 132.2 mg/L, which was improved by 11.2% compared with that in the control group.

TABLE 8

Effect of amount of added VB1 on ergothioneine accumulation by fermentation

| Amount of added VB1 in fermentation medium (g/L) | 0 (control group) | 0.01 | 0.05 | 0.1 | 0.2 | 0.4 | 0.8 |
|---|---|---|---|---|---|---|---|
| Content of ergothioneine in fermentation broth (mg/L) | 118.9 ± 2.37 | 122.7 ± 1.02 | 128.8 ± 2.41 | 132.2 ± 1.39 | 129.6 ± 2.67 | 127 ± 1.86 | 123.3 ± 3.03 |

TABLE 9

Effect of amount of added indolebutyric acid on ergothioneine accumulation by fermentation

| Amount of added indolebutyric acid in fermentation medium (mg/L) | 0 (control group) | 0.1 | 0.5 | 1 | 2 | 4 |
|---|---|---|---|---|---|---|
| Content of ergothioneine in fermentation broth (mg/L) | 128.6 ± 1.45 | 130.9 ± 2.23 | 138.4 ± 1.29 | 140.6 ± 3.09 | 137.7 ± 1.84 | 132.8 ± 0.93 |

Example 8: Addition of Indolebutyric Acid Improves Ergothioneine Accumulation by Fermentation The fermentation broths were prepared with soybean cake powder of 15 g/L as nitrogen source of the seed medium according to the same method as in Example 1, except for additionally adding indolebutyric acid of 0.1 mg/L, 0.5 mg/L, 1 mg/L, 2 mg/L, and 4 mg/L into the fermentation basal mediums, respectively, while the fermentation basal medium without indolebutyric acid was used as a control group. *Pleurotus ostreatus* mycelia CGMCC No. 6232 were subjected to fermentation and culture. After the fermentation, the contents of ergothioneine in the fermentation broths were determined, and the results were shown in Table 9.

The contents of ergothioneine in the fermentation broths were all higher than that in the control group, among which, when the amount of added indolebutyric acid was 1 mg/L, the content of ergothioneine was the highest and reached 140.6 mg/L, which was improved by 9.33% compared with that in the control group.

Example 9: Addition of Citric Acid Improves Ergothioneine Accumulation by Fermentation The fermentation broths were prepared with soybean cake powder of 15 g/L as nitrogen source of the seed medium according to the same method as in Example 1, except for additionally adding citric acid of 0.01 g/L, 0.05 g/L, 0.2 g/L, 0.4 g/L, and 0.8 g/L into the fermentation basal mediums, respectively, while the fermentation basal medium without citric acid was used as a control group. *Pleurotus ostreatus* mycelia CGMCC No. 6232 were subjected to fermentation and culture. After the fermentation, the contents of ergothioneine in the fermentation broths were determined, and the results were shown in Table 10.

The experimental results showed that when the amounts of added citric acid were in the range of 0.01 g/L-0.8 g/L, the contents of ergothioneine in the fermentation broths were all higher than that in the control group, among which, when the amount of added citric acid was 0.4 g/L, the content of ergothioneine was the highest and reached 138.3 mg/L, which was improved by 10.4% compared with that in the control group.

TABLE 10

Effect of amount of added citric acid on ergothioneine accumulation by fermentation

| Amount of added citric acid in fermentation medium (g/L) | 0 (control group) | 0.01 | 0.05 | 0.2 | 0.4 | 0.8 |
|---|---|---|---|---|---|---|
| Content of ergothioneine in fermentation broth (mg/L) | 125.3 ± 1.69 | 126.9 ± 2.75 | 130.2 ± 1.31 | 135.4 ± 0.83 | 138.3 ± 2.49 | 128.4 ± 1.16 |

Example 10: Addition of Pyruvic Acid Improves Ergothioneine Accumulation by Fermentation The fermentation broths were prepared with soybean cake powder of 15 g/L as nitrogen source of the seed medium according to the same method as in Example 1, except for additionally adding pyruvic acid of 0.05 g/L, 0.1 g/L, 0.5 g/L, 1.0 g/L, 2.2 g/L, and 4.5 g/L into the fermentation basal mediums, respectively, while the fermentation basal medium without pyruvic acid was used as a control group. *Pleurotus ostreatus* mycelia CGMCC No. 6232 were subjected to fermentation and culture. After the fermentation, the contents of ergothioneine in the fermentation broths were determined, and the results were shown in Table 11.

The experimental results showed that when the amounts of added pyruvic acid were in the range of 0.05 g/L-4.5 g/L, the contents of ergothioneine in the fermentation broths were all higher than that in the control group, among which, when the amount of added pyruvic acid was 2.2 g/L, the content of ergothioneine was the highest and reached 132.7 mg/L, which was improved by 5.9% compared with that in the control group.

according to the same method as in Example 1, except for additionally adding arginine of 0.1 g/L, 0.25 g/L, 0.75 g/L, 2 g/L, 5 g/L, and 7 g/L into the fermentation basal mediums, respectively, while the fermentation basal medium without arginine was used as a control group. *Pleurotus ostreatus* mycelia CGMCC No. 6232 were subjected to fermentation and culture. After the fermentation, the contents of ergothioneine in the fermentation broths were determined, and the results were shown in Table 12.

The experimental results showed that when the amounts of added arginine were in the range of 0.1 g/L-7 g/L, the contents of ergothioneine in the fermentation broths were all higher than that in the control group, among which, when the amount of added arginine was 2 g/L, the content of ergothioneine was the highest and reached 134.2 mg/L, which was improved by 12.7% compared with that in the control group.

TABLE 11

Effect of amount of added pyruvic acid on ergothioneine accumulation by fermentation

| Amount of added pyruvic acid in fermentation medium (g/L) | 0 (control group) | 0.05 | 0.1 | 0.5 | 1.0 | 2.2 | 4.5 |
|---|---|---|---|---|---|---|---|
| Content of ergothioneine in fermentation broth (mg/L) | 125.3 ± 1.69 | 127.4 ± 0.57 | 128.6 ± 1.03 | 130.4 ± 0.82 | 131.9 ± 1.43 | 132.7 ± 0.46 | 128.7 ± 0.69 |

Example 11: Addition of Arginine Improves Ergothioneine Accumulation by Fermentation The fermentation broths were prepared with soybean cake powder of 15 g/L as nitrogen source of the seed medium

TABLE 12

Effect of amount of added arginine on ergothioneine accumulation by fermentation

| Amount of added arginine in fermentation medium (g/L) | 0 (control group) | 0.1 | 0.25 | 0.75 | 2 | 5 | 7 |
|---|---|---|---|---|---|---|---|
| Content of ergothioneine in fermentation broth (mg/L) | 119.1 ± 3.47 | 126.4 ± 2.54 | 129.8 ± 3.01 | 131.7 ± 1.83 | 134.2 ± 2.66 | 132.9 ± 2.05 | 125.5 ± 1.24 |

TABLE 12-continued

Effect of amount of added arginine on ergothioneine accumulation by fermentation

Example 12: Addition of Lysine Improves Ergothioneine Accumulation by Fermentation The fermentation broths were prepared with soybean cake powder of 15 g/L as nitrogen source of the seed medium according to the same method as in Example 1, except for additionally adding lysine of 0.1 g/L, 0.25 g/L, 0.75 g/L, 2 g/L, 5 g/L, and 8 g/L into the fermentation basal mediums, respectively, while the fermentation basal medium without lysine was used as a control group. *Pleurotus ostreatus* mycelia CGMCC No. 6232 were subjected to fermentation and culture. After the fermentation, the contents of ergothioneine in the fermentation broths were determined, and the results were shown in Table 13.

The experimental results showed that when the amounts of added lysine were in the range of 0.1 g/L-8 g/L, the contents of ergothioneine in the fermentation broths were all higher than that in the control group, among which, when the amount of added lysine was 5 g/L, the content of ergothioneine was the highest and reached 135.1 mg/L, which was improved by 13.4% compared with that in the control group.

The experimental results showed that when the amounts of added leucine were in the range of 0.02 g/L-0.5 g/L, the contents of ergothioneine in the fermentation broths were all higher than that in the control group, among which, when the amount of added leucine was 0.1 g/L, the content of ergothioneine was the highest and reached 133.3 mg/L, which was improved by 11.9% compared with that in the control group.

TABLE 13

Effect of amount of added lysine on ergothioneine accumulation by fermentation

| Amount of added lysine in fermentation medium (g/L) | 0 (control group) | 0.1 | 0.25 | 0.75 | 2 | 5 | 8 |
|---|---|---|---|---|---|---|---|
| Content of ergothioneine in fermentation broth (mg/L) | 119.1 ± 3.47 | 124.8 ± 0.72 | 125.6 ± 2.03 | 128.9 ± 2.12 | 133.7 ± 1.51 | 135.1 ± 0.66 | 126.3 ± 2.67 |

Example 13: Addition of Leucine Improves Ergothioneine Accumulation by Fermentation The fermentation broths were prepared with soybean cake powder of 15 g/L as nitrogen source of the seed medium according to the same method as in Example 1, except for

TABLE 14

Effect of amount of added leucine on ergothioneine accumulation by fermentation

| Amount of added leucine in fermentation medium (g/L) | 0 (control group) | 0.02 | 0.05 | 0.1 | 0.25 | 0.5 |
|---|---|---|---|---|---|---|
| Content of ergothioneine in fermentation broth (mg/L) | 119.1 ± 3.47 | 127 ± 1.23 | 129.4 ± 2.17 | 133.3 ± 2.5 | 130.8 ± 2.46 | 125.5 ± 1.36 | additionally adding leucine of 0.02 g/L, 0.05 g/L, 0.1 g/L, 0.25 g/L, and 0.5 g/L into the fermentation basal mediums, respectively, while the fermentation basal medium without leucine was used as a control group. *Pleurotus ostreatus* mycelia CGMCC No. 6232 were subjected to fermentation and culture. After the fermentation, the contents of ergothioneine in the fermentation broths were determined, and the results were shown in Table 14.

Example 14: Addition of Aspartic Acid Improves Ergothioneine Accumulation by Fermentation The fermentation broths were prepared with soybean cake powder of 15 g/L as nitrogen source of the seed medium according to the same method as in Example 1, except for additionally adding aspartic acid of 0.05 g/L, 0.5 g/L, 1 g/L, 5 g/L, 7 g/L, and 9 g/L into the fermentation basal mediums, respectively, while the fermentation basal medium without aspartic acid was used as a control group. *Pleurotus ostreatus* mycelia CGMCC No. 6232 were subjected to fermentation and culture. After the fermentation, the contents of ergothioneine in the fermentation broths were determined, and the results were shown in Table 15.

The experimental results showed that when the amounts of added aspartic acid were in the range of 0.05 g/L-9 g/L, the contents of ergothioneine in the fermentation broths were all higher than that in the control group, among which, when the amount of added aspartic acid was 5 g/L, the content of ergothioneine was the highest and reached 135.9 mg/L, which was improved by 14.1% compared with that in the control group.

TABLE 15

Effect of amount of added aspartic acid on ergothioneine accumulation by fermentation

| Amount of added aspartic acid in fermentation medium (g/L) | 0 (control group) | 0.05 | 0.5 | 1 | 5 | 7 | 9 |
|---|---|---|---|---|---|---|---|
| Content of ergothioneine in fermentation broth (mg/L) | 119.1 ± 3.47 | 124.1 ± 3.07 | 128 ± 2.51 | 130.1 ± 4.28 | 135.9 ± 3.64 | 127.9 ± 2.59 | 123.8 ± 2.88 |

Example 15: Addition of Glutamic Acid Improves Ergothioneine Accumulation by Fermentation The fermentation broths were prepared with soybean cake powder of 15 g/L as nitrogen source of the seed medium according to the same method as in Example 1, except for additionally adding glutamic acid of 1 μmol/L, 5 μmol/L, 10 μmol/L, 50 μmol/L, and 100 μmol/L into the fermentation basal mediums, respectively, while the fermentation basal medium without glutamic acid was used as a control group. *Pleurotus ostreatus* mycelia CGMCC No. 6232 were subjected to fermentation and culture. After the fermentation, the contents of ergothioneine in the fermentation broths were determined, and the results were shown in Table 16.

The experimental results showed that when the amounts of added glutamic acid were in the range of 1 μmol/L-100 μmol/L, the contents of ergothioneine in the fermentation broths were all higher than that in the control group, among which, when the amount of added glutamic acid was 10 μmol/L, the content of ergothioneine was the highest and reached 131.2 mg/L, which was improved by 9.1% compared with that in the control group.

TABLE 16

Effect of amount of added glutamic acid on ergothioneine accumulation by fermentation

| Amount of added glutamic acid in fermentation medium (μmol/L) | 0 (control group) | 1 | 5 | 10 | 50 | 100 |
|---|---|---|---|---|---|---|
| Content of ergothioneine in fermentation broth (mg/L) | 120.2 ± 1.61 | 123.6 ± 0.92 | 128.8 ± 1.19 | 131.2 ± 2.62 | 124 ± 1.72 | 122.7 ± 1.63 |

Example 16: Addition of Betaine Improves Ergothioneine Accumulation by Fermentation The fermentation broths were prepared with soybean cake powder of 15 g/L as nitrogen source of the seed medium according to the same method as in Example 1, except for additionally adding betaine of 50 mmol/L, 100 mmol/L, 150 mmol/L, 200 mmol/L, and 250 mmol/L into the fermentation basal mediums, respectively, while the fermentation basal medium without betaine was used as a control group. *Pleurotus ostreatus* mycelia CGMCC No. 6232 were subjected to fermentation and culture. After the fermentation, the contents of ergothioneine in the fermentation broths were determined, and the results were shown in Table 17.

The experimental results showed that when the amounts of added betaine were in the range of 50 mmol/L-250 mmol/L, the contents of ergothioneine in the fermentation broths were all higher than that in the control group, among which, when the amount of added betaine was 150 mmol/L, the content of ergothioneine was the highest and reached 146.6 mg/L, which was improved by 22% compared with that in the control group.

TABLE 17

| Effect of amount of added betaine on ergothioneine accumulation by fermentation | | | | | | |
|---|---|---|---|---|---|---|
| Amount of added betaine in fermentation medium (mmol/L) | 0 (control group) | 50 | 100 | 150 | 200 | 250 |
| Content of ergothioneine in fermentation broth (mg/L) | 120.2 ± 1.61 | 125.3 ± 2.67 | 130.1 ± 2.14 | 146.6 ± 2.64 | 129.9 ± 3.34 | 124.8 ± 1.38 |

Example 17: Addition of Histidine Improves Ergothioneine Accumulation by Fermentation The fermentation broths were prepared with soybean cake powder of 15 g/L as nitrogen source of the seed medium according to the same method as in Example 1, except for additionally adding histidine of 0.1 mmol/L, 0.5 mmol/L, 1 mmol/L, 2 mmol/L, and 3 mmol/L into the fermentation basal mediums, respectively, while the fermentation basal medium without histidine was used as a control group. *Pleurotus ostreatus* mycelia CGMCC No. 6232 were subjected to fermentation and culture. After the fermentation, the contents of ergothioneine in the fermentation broths were determined, and the results were shown in Table 18.

The experimental results showed that when the amounts of added histidine were in the range of 0.1 mmol/L-3 mmol/L, the contents of ergothioneine in the fermentation broths were all higher than that in the control group, among which, when the amount of added histidine was 1 mmol/L, the content of ergothioneine was the highest and reached 129.5 mg/L, which was improved by 7.7% compared with that in the control group.

mmol/L, 25 mmol/L, 35 mmol/L, and 45 mmol/L into the fermentation basal mediums, respectively, while the fermentation basal medium without cysteine was used as a control group. *Pleurotus ostreatus* mycelia CGMCC No. 6232 were subjected to fermentation and culture. After the fermentation, the contents of ergothioneine in the fermentation broths were determined, and the results were shown in Table 19.

The experimental results showed that when the amounts of added cysteine were in the range of 2 mmol/L-45 mmol/L, the contents of ergothioneine in the fermentation broths were all higher than that in the control group, among which, when the amount of added cysteine was 15 mmol/L, the content of ergothioneine was the highest and reached 175.5 mg/L, which was improved by 46% compared with that in the control group.

TABLE 18

| Effect of amount of added histidine on ergothioneine accumulation by fermentation | | | | | | |
|---|---|---|---|---|---|---|
| Amount of added histidine in fermentation medium (mmol/L) | 0 (control group) | 0.1 | 0.5 | 1 | 2 | 3 |
| Content of ergothioneine in fermentation broth (mg/L) | 120.2 ± 1.61 | 122.9 ± 1.24 | 129 ± 4.32 | 129.5 ± 3.22 | 128.8 ± 2.39 | 122.1 ± 1.82 |

Example 18: Addition of Cysteine Improves Ergothioneine Accumulation by Fermentation The fermentation broths were prepared with soybean cake powder of 15 g/L as nitrogen source of the seed medium according to the same method as in Example 1, except for additionally adding cysteine of 2 mmol/L, 9 mmol/L, 15

TABLE 19

| Effect of amount of added cysteine on ergothioneine accumulation by fermentation | | | | | | | |
|---|---|---|---|---|---|---|---|
| Amount of added cysteine in fermentation medium (mmol/L) | 0 (control group) | 2 | 9 | 15 | 25 | 35 | 45 |
| Content of ergothioneine in fermentation broth (mg/L) | 120.2 ± 1.61 | 124.8 ± 2.03 | 140.4 ± 1.83 | 175.5 ± 1.36 | 164.6 ± 4.31 | 148.1 ± 2.74 | 126.1 ± 2.99 |

Example 19: Effect of Timing for Adding Cysteine on Ergothioneine Accumulation by Fermentation The fermentation broths were prepared with soybean cake powder of 15 g/L as nitrogen source of the seed medium according to the same method as in Example 1, except for additionally adding cysteine of 15 mmol/L into the fermentation basal medium before the fermentation and into the fermentation broth on the $2^{nd}$, $4^{th}$, $6^{th}$, $8^{th}$, and $10^{th}$ day, respectively, while the fermentation basal medium without cysteine was used as a control group. *Pleurotus ostreatus* mycelia CGMCC No. 6232 were subjected to fermentation and culture. After the fermentation, the contents of ergothioneine in the fermentation broths were determined, and the results were shown in Table 20.

TABLE 21

Effect of amount of added methionine on ergothioneine accumulation by fermentation

| Amount of added methionine in fermentation medium (mmol/L) | 0 (control group) | 3 | 9 | 15 | 25 | 35 | 45 |
|---|---|---|---|---|---|---|---|
| Content of ergothioneine in fermentation broth (mg/L) | 120.2 ± 1.61 | 127.3 ± 3.47 | 154.8 ± 3.31 | 179.6 ± 4.17 | 168.5 ± 4.53 | 153.7 ± 3.2 | 126.9 ± 2.81 |

The experimental results showed that adding cysteine before the fermentation and to the $10^{th}$ day of the fermentation may all improve the accumulation of ergothioneine, and when cysteine was added on the $6^{th}$ day of fermentation, the content of ergothioneine in the fermentation broth was the highest and reached 193.8 mg/L, which was improved by 60% compared with that in the control group.

TABLE 20

Effect of timing for adding cysteine on ergothioneine accumulation by fermentation

| Timing for adding cysteine (d) | control group | 0 | 2 | 4 | 6 | 8 | 10 |
|---|---|---|---|---|---|---|---|
| Content of ergothioneine in fermentation broth (mg/L) | 120.2 ± 1.61 | | | 162.33 | 186.1 ± 1.67 | 193.8 ± 4.16 | 172.1 ± 1.73 | 156.5 ± 2.52 |

Example 20: Addition of Methionine Improves Ergothioneine Accumulation by Fermentation The fermentation broths were prepared with soybean cake powder of 15 g/L as nitrogen source of the seed medium according to the same method as in Example 1, except for additionally adding methionine of 3 mmol/L, 9 mmol/L, 15 mmol/L, 25 mmol/L, 35 mmol/L, and 45 mmol/L into the fermentation basal mediums, respectively, while the fermentation basal medium without methionine was used as a control group. *Pleurotus ostreatus* mycelia CGMCC No. 6232 were subjected to fermentation and culture. After the fermentation, the contents of ergothioneine in the fermentation broths were determined, and the results were shown in Table 21.

The experimental results showed that when the amounts of added methionine were in the range of 3 mmol/L-45 mmol/L, the contents of ergothioneine in the fermentation broths were all higher than that in the control group, among which, when the amount of added methionine was 15 mmol/L, the content of ergothioneine was the highest and reached 179.6 mg/L, which was improved by 49.4% compared with that in the control group.

Example 21: Effect of Timing for Adding Methionine on Ergothioneine Accumulation by Fermentation The fermentation broths were prepared with soybean cake powder of 15 g/L as nitrogen source of the seed medium according to the same method as in Example 1, except for additionally adding methionine of 15 mmol/L into the fermentation basal medium before the fermentation and into the fermentation broth on the $2^{nd}$, $4^{th}$, $6^{th}$, $8^{th}$, and $10^{th}$ day, respectively, while the fermentation basal medium without methionine was used as a control group. *Pleurotus ostreatus* mycelia CGMCC No. 6232 were subjected to fermentation and culture. After the fermentation, the contents of ergothioneine in the fermentation broths were determined, and the results were shown in Table 22.

The experimental results showed that adding methionine before the fermentation and to the $10^{th}$ day of the fermentation may all improve the accumulation of ergothioneine, and when methionine was added on the $4^{th}$ day of fermentation, the content of ergothioneine in the fermentation broth was the highest and reached 202.6 mg/L, which was improved by 63.1% compared with that in the control group.

TABLE 22

| Effect of timing for methionine on ergothioneine accumulation by fermentation | | | | | | | |
|---|---|---|---|---|---|---|---|
| Timing for adding methionine (d) | control group | 0 | 2 | 4 | 6 | 8 | 10 |
| Content of ergothioneine in fermentation broth (mg/L) | 124.2 ± 2.65 | 179.3 ± 4.23 | 190.5 ± 2.84 | 202.6 ± 5.01 | 174.9 ± 3.73 | 160.3 ± 5.29 | 149.3 ± 3.27 |

Example 22: Addition of Composition of Amino Acids Improves Ergothioneine Accumulation by Fermentation The fermentation broths were prepared with soybean cake powder of 15 g/L as nitrogen source of the seed medium according to the same method as in Example 1, except for additionally adding a composition of "15 mmol/L methionine+1 mmol/L histidine" into the fermentation basal medium before the fermentation and into the fermentation broth on the $2^{nd}$, $4^{th}$, $6^{th}$, and $8^{th}$ day, respectively, while the fermentation basal medium without the composition of amino acids was used as a control group. *Pleurotus ostreatus* mycelia CGMCC No. 6232 were subjected to fermentation and culture. After the fermentation, the contents of ergothioneine in the fermentation broths were determined, and the results were shown in Table 23.

The experimental results showed that adding the composition of methionine and histidine before the fermentation and in the process of fermentation may both improve the accumulation of ergothioneine, and when the composition of amino acids was added before the fermentation, the content of ergothioneine in the fermentation broth was the highest and reached 179.8 mg/L, which was improved by 51.9% compared with that in the control group.

according to the same method as in Example 1, except for additionally adding a composition of "15 mmol/L cysteine+1 mmol/L histidine" into the fermentation basal mediums before the fermentation and into the fermentation broth on the $2^{nd}$, $4^{th}$, $6^{th}$, and $8^{th}$ day, respectively, while the fermentation basal medium without the composition of amino acids was used as a control group. *Pleurotus ostreatus* mycelia CGMCC No. 6232 were subjected to fermentation and culture. After the fermentation, the contents of ergothioneine in the fermentation broths were determined, and the results were shown in Table 24.

The experimental results showed that adding the composition of cysteine and histidine before the fermentation and in the process of fermentation may both improve the accumulation of ergothioneine, and when the composition of amino acids was added before the fermentation, the content of ergothioneine in the fermentation broth was the highest and reached 168.2 mg/L, which was improved by 42.1% compared with that in the control group.

TABLE 23

| Effect of timing for adding methionine and histidine on ergothioneine accumulation by fermentation | | | | | | |
|---|---|---|---|---|---|---|
| Timing for adding methionine and histidine (d) | control group | 0 | 2 | 4 | 6 | 8 |
| Content of ergothioneine in fermentation broth (mg/L) | 118.4 ± 2.12 | 179.8 ± 3.85 | 162.2 ± 3.17 | 160.9 ± 4.03 | 147.1 ± 3.26 | 130.7 ± 4.54 |

Example 23: Addition of Composition of Amino Acids Improves Ergothioneine Accumulation by Fermentation The fermentation broths were prepared with soybean cake powder of 15 g/L as nitrogen source of the seed medium

TABLE 24

| Effect of timing for adding cysteine and histidine on ergothioneine accumulation by fermentation | | | | | | |
|---|---|---|---|---|---|---|
| Timing for adding cysteine and histidine (d) | control group | 0 | 2 | 4 | 6 | 8 |
| Content of ergothioneine in fermentation broth (mg/L) | 118.4 ± 2.12 | 168.2 ± 3.47 | 147.4 ± 3.63 | 149.1 ± 4.21 | 136.5 ± 3.78 | 128.6 ± 4.16 |

Example 24: Addition of Composition of Amino Acids Improves Ergothioneine Accumulation by Fermentation The fermentation broths were prepared with soybean cake powder of 15 g/L as nitrogen source of the seed medium according to the same method as in Example 1, except for additionally adding compositions of "15 mmol/L methionine+15 mmol/L cysteine" and "7.5 mmol/L methionine+7.5 mmol/L cysteine" into the fermentation basal mediums before the fermentation and into the fermentation broths on the $2^{nd}$, $4^{th}$, $6^{th}$, and $8^{th}$ day, respectively, while the fermentation basal medium without the compositions of amino acids was used as a control group. *Pleurotus ostreatus* mycelia CGMCC No. 6232 were subjected to fermentation and culture. After the fermentation, the contents of ergothioneine in the fermentation broths were determined, and the results were shown in Table 25 and Table 26.

The experimental results showed that adding the composition of methionine and cysteine before the fermentation and in the process of fermentation may both improve the accumulation of ergothioneine, and when 7.5 mmol/L methionine and 7.5 mmol/L cysteine were added before the fermentation, the content of ergothioneine in the fermentation broth was the highest and reached 208.3 mg/L, which was improved by 75.9% compared with that in the control group.

according to the same method as in Example 1, except for additionally adding compositions of "15 mmol/L methionine+15 mmol/L cysteine+1 mmol/L histidine" and "7.5 mmol/L methionine+7.5 mmol/L cysteine+1 mmol/L histidine" into the fermentation basal medium before the fermentation and into the fermentation broth on the $2^{nd}$, $4^{th}$, $6^{th}$, and $8^{th}$ day, respectively, while the fermentation basal medium without the composition of amino acids was used as a control group. *Pleurotus ostreatus* mycelia CGMCC No. 6232 were subjected to fermentation and culture. After the fermentation, the contents of ergothioneine in the fermentation broths were determined, and the results were shown in Table 27 and Table 28.

The experimental results showed that adding the composition of methionine, cysteine and histidine before the fermentation and in the process of fermentation may both improve the accumulation of ergothioneine, and when 7.5 mmol/L methionine, 7.5 mmol/L cysteine and 1 mmol/L histidine were added before the fermentation, the content of ergothioneine in the fermentation broth was the highest and reached 206.8 mg/L, which was improved by 74.6% compared with that in the control group.

TABLE 25

Effect of timing for adding methionine and cysteine on ergothioneine accumulation by fermentation

| Timing for adding 15 mmol/L methionine and 15 mmol/L cysteine (d) | control group | 0 | 2 | 4 | 6 | 8 |
|---|---|---|---|---|---|---|
| Content of ergothioneine in fermentation broth (mg/L) | 118.4 ± 2.12 | 189.1 ± 2.59 | 177.7 ± 2.58 | 163.5 ± 3.19 | 149.2 ± 4.12 | 130.1 ± 2.43 |

TABLE 26

Effect of timing for adding methionine and cysteine on ergothioneine accumulation by fermentation

| Timing for adding 7.5 mmol/L methionine and 7.5 mmol/L cysteine (d) | control group | 0 | 2 | 4 | 6 | 8 |
|---|---|---|---|---|---|---|
| Content of ergothioneine in fermentation broth (mg/L) | 118.4 ± 2.12 | 208.3 ± 3.76 | 175.9 ± 3.3 | 169.2 ± 3.88 | 145.8 ± 4.26 | 132.3 ± 2.92 |

Example 25: Addition of Composition of Amino Acids Improves Ergothioneine Accumulation by Fermentation The fermentation broths were prepared with soybean cake powder of 15 g/L as nitrogen source of the seed medium

TABLE 27

Effect of timing for adding methionine, cysteine and histidine on ergothioneine accumulation by fermentation

| Timing for adding 15 mmol/L methionine, 15 mmol/L cysteine and 1 mmol/L histidine (d) | control group | 0 | 2 | 4 | 6 | 8 |
|---|---|---|---|---|---|---|
| Content of ergothioneine in fermentation broth (mg/L) | 118.4 ± 2.12 | 185.8 ± 3.42 | 163.3 ± 3.02 | 155.6 ± 2.85 | 143.6 ± 3.06 | 127.1 ± 1.73 |

TABLE 28

Effect of timing for adding methionine, cysteine and histidine on ergothioneine accumulation by fermentation

| Timing for adding 7.5 mmol/L methionine, 7.5 mmol/L cysteine and 1 mmol/L histidine (d) | control group | 0 | 2 | 4 | 6 | 8 |
|---|---|---|---|---|---|---|
| Content of ergothioneine in fermentation broth (mg/L) | 118.4 ± 2.12 | 206.8 ± 2.34 | 180.7 ± 2.64 | 172.4 ± 4.11 | 151.3 ± 3.92 | 129.7 ± 3.25 |

Example 26: Addition of Tween 60 Improves Ergothioneine Accumulation by Fermentation The fermentation broths were prepared with soybean cake powder of 15 g/L as nitrogen source of the seed medium according to the same method as in Example 1, except for additionally adding tween 60 of 2 g/L, 5 g/L, 10 g/L, 20 g/L, 40 g/L, and 50 g/L into the fermentation basal mediums, respectively, while the fermentation basal medium without tween 60 was used as a control group. *Pleurotus ostreatus* mycelia CGMCC No. 6232 were subjected to fermentation and culture. After the fermentation, the contents of ergothioneine in the fermentation broths were determined, and the results were shown in Table 29.

The experimental results showed that when the amounts of added tween 60 were in the range of 2 g/L-50 g/L, the contents of ergothioneine in the fermentation broths were all higher than that in the control group, among which, when the amount of added tween 60 was 10 g/L, the content of ergothioneine was the highest and reached 212.7 mg/L, which was improved by 74.9% compared with that in the control group.

In addition, the contents of extracellular ergothioneine in the filtrates were also determined, and it was found that addition of tween 60 at the above concentrations may all improve the contents of extracellular ergothioneine, among which, when the added amount was 5 g/L, the content of extracellular ergothioneine in the filtrate was the highest and reached 16.24 mg/L, which was improved by 86% compared with 8.73 mg/L in the control group.

Example 27: Addition of Tween 80 Improves Ergothioneine Accumulation by Fermentation The fermentation broths were prepared with soybean cake powder of 15 g/L as nitrogen source of the seed medium according to the same method as in Example 1, except for additionally adding tween 80 of 0.5 g/L, 2 g/L, 5 g/L, 10 g/L, 20 g/L, and 40 g/L into the fermentation basal mediums, respectively, while the fermentation basal medium without tween 80 was used as a control group. *Pleurotus ostreatus* mycelia CGMCC No. 6232 were subjected to fermentation and culture. After the fermentation, the contents of ergothioneine in the fermentation broths were determined, and the results were shown in Table 30.

The experimental results showed that when the amounts of added tween 80 were in the range of 0.5 g/L-40 g/L, the contents of ergothioneine in the fermentation broths were all higher than that in the control group, among which, when the amount of added tween 80 was 10 g/L, the content of

TABLE 29

Effect of amount of added tween 60 on ergothioneine accumulation by fermentation

| Amount of added tween 60 in fermentation medium (g/L) | 0 (control group) | 2 | 5 | 10 | 20 | 40 | 50 |
|---|---|---|---|---|---|---|---|
| Content of ergothioneine in fermentation broth (mg/L) | 121.6 ± 2.58 | 128.8 ± 1.51 | 173.6 ± 2.98 | 212.7 ± 4.52 | 184.4 ± 3.78 | 154.2 ± 2.63 | 129.1 ± 2.1 | ergothioneine was the highest and reached 217 mg/L, which was improved by 78.5% compared with that in the control group.

TABLE 30

Effect of amount of added tween 80 on ergothioneine accumulation by fermentation

| Amount of added tween 80 in fermentation medium (g/L) | 0 (control group) | 0.5 | 2 | 5 | 10 | 20 | 40 |
|---|---|---|---|---|---|---|---|
| Content of ergothioneine in fermentation broth (mg/L) | 121.6 ± 2.58 | 130.2 ± 1.56 | 155.9 ± 2.7 | 181.8 ± 3.95 | 217 ± 4.37 | 170.9 ± 4.43 | 130.9 ± 1.61 |

In addition, the contents of extracellular ergothioneine in the filtrates were also determined, and it was found that addition of tween 80 at the above concentrations may all improve the contents of extracellular ergothioneine, among which, when the added amount was 10 g/L, the content of extracellular ergothioneine in the filtrate was the highest and reached 18.72 mg/L, which was improved by 114.4% compared with 8.73 mg/L in the control group.

Example 28: Addition of Span 80 Improves Ergothioneine Accumulation by Fermentation The fermentation broths were prepared with soybean cake powder of 15 g/L as nitrogen source of the seed medium according to the same method as in Example 1, except for additionally adding span 80 of 0.2 g/L, 0.5 g/L, 1 g/L, 3 g/L, 5 g/L, and 10 g/L into the fermentation basal mediums, respectively, while the fermentation basal medium without span 80 was used as a control group. *Pleurotus ostreatus* mycelia CGMCC No. 6232 were subjected to fermentation and culture. After the fermentation, the contents of ergothioneine in the fermentation broths were determined, and the results were shown in Table 31.

The experimental results showed that when the amounts of added span 80 were in the range of 0.2 g/L-10 g/L, the contents of ergothioneine in the fermentation broths were all higher than that in the control group, among which, when the amount of added span 80 was 3 g/L, the content of ergothioneine was the highest and reached 196.5 mg/L, which was improved by 69.7% compared with that in the control group.

TABLE 31

Effect of amount of added span 80 on ergothioneine accumulation by fermentation

| Amount of added span 80 in fermentation medium (g/L) | 0 (control group) | 0.2 | 0.5 | 1 | 3 | 5 | 10 |
|---|---|---|---|---|---|---|---|
| Content of ergothioneine in fermentation broth (mg/L) | 115.8 ± 1.79 | 124.7 ± 2.59 | 156.3 ± 1.92 | 175.1 ± 2.83 | 196.5 ± 3.54 | 184.3 ± 3.7 | 129.6 ± 1.18 |

Example 29: Addition of Chitosan Improves Ergothioneine Accumulation by Fermentation The fermentation broths were prepared with soybean cake powder of 15 g/L as nitrogen source of the seed medium according to the same method as in Example 1, except for additionally adding chitosan of 0.2 g/L, 0.25 g/L, 0.3 g/L, 0.35 g/L, and 0.4 g/L into the fermentation basal mediums, respectively, while the fermentation basal medium without chitosan was used as a control group. *Pleurotus ostreatus* mycelia CGMCC No. 6232 were subjected to fermentation and culture. After the fermentation, the contents of ergothioneine in the fermentation broths were determined, and the results were shown in Table 32.

The experimental results showed that when the amounts of added chitosan were in the range of 0.2 g/L-0.4 g/L, the contents of ergothioneine in the fermentation broths were all higher than that in the control group, among which, when the amount of added chitosan was 0.3 g/L, the content of ergothioneine was the highest and reached 128.8 mg/L, which was improved by 11.2% compared with that in the control group.

TABLE 32

| Effect of amount of added chitosan on ergothioneine accumulation by fermentation | | | | | | |
|---|---|---|---|---|---|---|
| Amount of added chitosan in fermentation medium (g/L) | 0 (control group) | 0.2 | 0.25 | 0.3 | 0.35 | 0.4 |
| Content of ergothioneine in fermentation broth (mg/L) | 115.8 ± 1.79 | 122.9 ± 1.03 | 126.1 ± 0.84 | 128.8 ± 0.02 | 126.4 ± 0.97 | 123.3 ± 0.6 |

Example 30: Addition of Fluconazole Improves Ergothioneine Accumulation by Fermentation The fermentation broths were prepared with soybean cake powder of 15 g/L as nitrogen source of the seed medium according to the same method as in Example 1, except for additionally adding Fluconazole of 2 mg/L, 5 mg/L, 20 mg/L, 50 mg/L, and 80 mg/L into the fermentation basal mediums, respectively, while the fermentation basal medium without Fluconazole was used as a control group. *Pleurotus ostreatus* mycelia CGMCC No. 6232 were subjected to fermentation and culture. After the fermentation, the contents of ergothioneine in the fermentation broths were determined, and the results were shown in Table 33.

The experimental results showed that when the amounts of added Fluconazole were in the range of 2 mg/L-80 mg/L, the contents of ergothioneine in the fermentation broths were all higher than that in the control group, among which, when the amount of added Fluconazole was 50 mg/L, the content of ergothioneine was the highest and reached 146.4 mg/L, which was improved by 19.6% compared with that in the control group.

TABLE 33

| Effect of amount of added Fluconazole on ergothioneine accumulation by fermentation | | | | | | |
|---|---|---|---|---|---|---|
| Amount of added Fluconazole in fermentation medium (mg/L) | 0 (control group) | 2 | 5 | 20 | 50 | 80 |
| Content of ergothioneine in fermentation broth (mg/L) | 122.4 ± 2.81 | 131.6 ± 1.92 | 137.2 ± 2.51 | 141.3 ± 3.27 | 146.4 ± 3.41 | 132.7 ± 3.39 |

In addition, the contents of extracellular ergothioneine in the filtrates were also determined, and it was found that addition of Fluconazole at the above concentrations may all improve the contents of extracellular ergothioneine, among which, when the added amount was 50 mg/L, the content of extracellular ergothioneine in the filtrate was the highest and reached 7.67 mg/L, which was improved by 169.1% compared with 2.85 mg/L in the control group.

Example 31: Addition of Miconazole Improves Ergothioneine Accumulation by Fermentation The fermentation broths were prepared with soybean cake powder of 15 g/L as nitrogen source of the seed medium according to the same method as in Example 1, except for additionally adding Miconazole of 0.5 mg/L, 1 mg/L, 5 mg/L, 10 mg/L, 15 mg/L and 50 mg/L into the fermentation basal mediums, respectively, while the fermentation basal medium without Miconazole was used as a control group. *Pleurotus ostreatus* mycelia CGMCC No. 6232 were subjected to fermentation and culture. After the fermentation, the contents of ergothioneine in the fermentation broths were determined, and the results were shown in Table 34.

The experimental results showed that when the amounts of added Miconazole were in the range of 0.5 mg/L-15 mg/L, the contents of ergothioneine in the fermentation broths were all higher than that in the control group, among which, when the amount of added Miconazole was 5 mg/L, the content of ergothioneine was the highest and reached 152.9 mg/L, which was improved by 24.9% compared with that in the control group.

TABLE 34

| Effect of amount of added Miconazole on ergothioneine accumulation by fermentation | | | | | | |
|---|---|---|---|---|---|---|
| Amount of added Miconazole in fermentation medium (mg/L) | 0 (control group) | 0.5 | 1 | 5 | 10 | 15 |
| Content of ergothioneine in fermentation broth (mg/L) | 122.4 ± 2.81 | 132.4 ± 2.96 | 140.0 ± 3.28 | 152.9 ± 4.22 | 147.0 ± 3.09 | 129.8 ± 2.11 |

In addition, the contents of extracellular ergothioneine in the filtrates were also determined, and it was found that addition of Miconazole at the above concentrations may all improve the contents of extracellular ergothioneine, among which, when the added amount was 50 mg/L, the content of extracellular ergothioneine in the filtrate was the highest and reached 9.14 mg/L, which was improved by 220.4% compared with 2.85 mg/L in the control group.

Example 32: Addition of Ketoconazole Improves Ergothioneine Accumulation by Fermentation The fermentation broths were prepared with soybean cake powder of 15 g/L as nitrogen source of the seed medium according to the same method as in Example 1, except for additionally adding Ketoconazole of 0.5 mg/L, 1 mg/L, 5 mg/L, 10 mg/L, and 50 mg/L into the fermentation basal mediums, respectively, while the fermentation basal medium without Ketoconazole was used as a control group. *Pleurotus ostreatus* mycelia CGMCC No. 6232 were subjected to fermentation and culture. After the fermentation, the contents of ergothioneine in the fermentation broths were determined, and the results were shown in Table 35.

The experimental results showed that when the amounts of added Ketoconazole were in the range of 0.5 mg/L-50 mg/L, the contents of ergothioneine in the fermentation broths were all higher than that in the control group, among which, when the amount of added Ketoconazole was 5 mg/L, the content of ergothioneine was the highest and reached 134.1 mg/L, which was improved by 9.6% compared with that in the control group.

Example 33: Addition of Compositions Improves Ergothioneine Accumulation by Fermentation The fermentation broths were prepared with soybean cake powder of 15 g/L as nitrogen source of the seed medium according to the same method as in Example 1, except for additionally adding three different compositions of "4 g/L $NH_4Cl$+0.64 g/L folic acid", "4 g/L $NH_4Cl$+0.64 g/L folic acid+0.1 g/L VB1", and "7.5 mmol/L methionine+7.5 mmol/L cysteine" into the fermentation basal mediums, respectively, while the fermentation basal medium without the compositions was used as a control group. *Pleurotus ostreatus* mycelia CGMCC No. 6232 were subjected to fermentation and culture. After the fermentation, the contents of ergothioneine in the fermentation broths were determined, and the results were shown in Table 36.

The experimental results showed that the addition of the three compositions improves the accumulation of ergothioneine, and the contents of ergothioneine in the fermentation broths were all higher than that in the control group, among which, when the composition of "7.5 mmol/L methionine+ 7.5 mmol/L cysteine" was added, the content of ergothioneine was the highest and reached 210.7 mg/L, which was improved by 80.2% compared with that in the control group.

TABLE 35

Effect of amount of added Ketoconazole on ergothioneine accumulation by fermentation

| Amount of added Ketoconazole in fermentation medium (mg/L) | 0 (control group) | 0.5 | 1 | 5 | 10 | 50 |
|---|---|---|---|---|---|---|
| Content of ergothioneine in fermentation broth (mg/L) | 122.4 ± 2.81 | 127.6 ± 1.06 | 130.7 ± 2.22 | 134.1 ± 2.99 | 132.5 ± 1.87 | 128.9 ± 1.18 |

In addition, the contents of extracellular ergothioneine in the filtrates were also determined, and it was found that

TABLE 36

Effect of addition of compositions on ergothioneine accumulation by fermentation

| Addition of compositions in fermentation medium | 0 (control group) | 4 g/L $NH_4Cl$ + 0.64 g/L folic acid | 4 g/L $NH_4Cl$ + 0.64 g/L folic acid + 0.1 g/L VB1 | 7.5 mmol/L methionine + 7.5 mmol/L cysteine |
|---|---|---|---|---|
| Content of ergothioneine in fermentation broth (mg/L) | 116.9 ± 3.02 | 140.4 ± 2.74 | 127.5 ± 3.6 | 210.7 ± 4.11 | addition of Ketoconazole at the above concentrations may all improve the contents of extracellular ergothioneine, among which, when the added amount was 50 mg/L, the content of extracellular ergothioneine in the filtrate was the highest and reached 5.77 mg/L, which was improved by 102.5% compared with 2.85 mg/L in the control group.

Example 34: Increasing the Content of Casein Peptone in the Medium Improves Ergothioneine Accumulation by Fermentation The fermentation broths were prepared with soybean cake powder of 15 g/L as nitrogen source of the seed medium according to the same method as in Example 1, except for increasing the content of casein peptone in the fermentation basal medium to 40 g/L, 50 g/L, 60 g/L, 70 g/L and 80 g/L, respectively, while the fermentation basal medium containing 35 g/L of casein peptone was used as a control group. *Pleurotus ostreatus* mycelia CGMCC No. 6232 were subjected to fermentation and culture. After the fermentation, the contents of ergothioneine in the fermentation broths were determined, and the results were shown in Table 37.

The experimental results showed that when the contents of casein peptone in the mediums were in the range of 40 g/L-80 g/L, the contents of ergothioneine in the fermentation broths were all higher than that in the control group, among which, when the amount of added casein peptone was 50 g/L, the content of ergothioneine was the highest and reached 157.5 mg/L, which was improved by 33.6% compared with that in the control group.

TABLE 37

Effect of content of casein peptone in the medium on ergothioneine accumulation by fermentation

| Content of casein peptone in fermentation medium (g/L) | 35 (control group) | 40 | 50 | 60 | 70 | 80 |
|---|---|---|---|---|---|---|
| Content of ergothioneine in fermentation broth (mg/L) | 117.9 ± 1.81 | 128.2 ± 2.02 | 157.5 ± 3.13 | 149.8 ± 3.56 | 143.1 ± 4.36 | 126.9 ± 2.43 |

Example 35: Increasing Content of Glycerol in the Medium Improves Ergothioneine Accumulation by Fermentation The fermentation broths were prepared with soybean cake powder of 15 g/L as nitrogen source of the seed medium according to the same method as in Example 1, except for adjusting the content of casein peptone to 50 g/L in the fermentation basal medium, while increasing the content of glycerol to 65 g/L, 75 g/L, 85 g/L and 95 g/L, respectively in the fermentation basal medium, and the fermentation basal medium with 50 g/L of casein peptone and 50 g/L of glycerol was used as a control group. *Pleurotus ostreatus* mycelia CGMCC No. 6232 were subjected to fermentation and culture. After the fermentation, the contents of ergothioneine in the fermentation broths were determined, and the results were shown in Table 38.

The experimental results showed that when the contents of glycerol were in the range of 65 g/L-95 g/L in the medium, the contents of ergothioneine in the fermentation broths were all higher than that in the control group, among which, when the content of glycerol was 75 g/L, the content of ergothioneine was the highest and reached 170.2 mg/L, which was improved by 8.5% compared with that in the control group.

Example 36: Addition of Composition of Methionine and Cysteine Improves Ergothioneine Accumulation by Fermentation The fermentation broths were prepared with soybean cake powder of 15 g/L as nitrogen source of the seed medium according to the same method as in Example 1, except for adjusting the content of glycerol to 75 g/L and the content of casein peptone to 50 g/L in the fermentation basal medium, then additionally adding compositions of methionine and cysteine with different concentrations to the fermentation basal medium respectively, while the fermentation basal medium, without the compositions, with glycerol content adjusted to 75 g/L and casein peptone content adjusted to 50 g/L was used as a control group. *Pleurotus ostreatus* mycelia CGMCC No. 6232 were subjected to fermentation and culture. After the fermentation, the contents of ergothioneine in the fermentation broths were determined, and the results were shown in Table 39.

The experimental results showed that addition of compositions consisting of methionine and cysteine at different concentrations improves the accumulation of ergothioneine, and the contents of ergothioneine in the fermentation broths were all higher than that in the control group, among which, when the composition consisting of "14 mmol/L methionine+7.5 mmol/L cysteine" was added, the content of ergothioneine in the fermentation broth was the highest and reached 315.7 mg/L, which was improved by 82.1% compared with that in the control group.

TABLE 38

Effect of content of glycerol in the medium on ergothioneine accumulation by fermentation

| Content of glycerol in fermentation medium (g/L) | 50 (control group) | 65 | 75 | 85 | 95 |
|---|---|---|---|---|---|
| Content of ergothioneine in fermentation broth (mg/L) | 156.8 ± 1.26 | 162.4 ± 2.67 | 170.2 ± 3.49 | 164.8 ± 3.41 | 160.1 ± 1.15 |

TABLE 39

Effect of amount of added composition consisting of methionine and cysteine on ergothioneine accumulation by fermentation

| Amount of added composition consisting of methionine and cysteine in the medium | 0 (control group) | 7.5 mmol/L methionine + 7.5 mmol/L cysteine | 9.5 mmol/L methionine + 7.5 mmol/L cysteine | 9.5 mmol/L methionine + 9.5 mmol/L cysteine | 12.5 mmol/L methionine + 7.5 mmol/L cysteine | 14 mmol/L methionine + 7.5 mmol/L cysteine |
|---|---|---|---|---|---|---|
| Content of ergothioneine in fermentation broth (mg/L) | 173.4 ± 4.07 | 242.4 ± 3.69 | 259.6 ± 2.65 | 261.2 ± 3.91 | 278.5 ± 3.12 | 315.7 ± 2.84 |

Example 37: Adjustment of Temperature in the Process of Fermentation Improves Ergothioneine Accumulation by Fermentation The fermentation broths were prepared with soybean cake powder of 15 g/L as nitrogen source of the seed medium according to the same method as in Example 1, except for properly adjusting the temperature of fermentation in the process of fermentation, while the test group with an initial temperature of 25° C. and under thermostatical control in the process of fermentation was used as a control group. *Pleurotus ostreatus* mycelia CGMCC No. 6232 were subjected to fermentation and culture. After the fermentation, the contents of ergothioneine in the fermentation broths were determined, and the results were shown in Table 40. In Table 40, for example, the data in the column in which adjustment time (days) was "0-4-12-15" and adjustment temperature (° C.) was "25-28-31" indicates the result in which the temperature was 25° C. in 0-3 days, 28° C. in 4-11 days and 31° C. in 12-15 days. The other columns were illustrated in a similar manner.

The experimental results showed that properly adjusting the temperature in the process of fermentation improves the accumulation of ergothioneine, and the contents of ergothioneine in the fermentation broths were all higher than that in the control group.

*ostreatus* mycelia CGMCC No. 6232 were subjected to fermentation and culture. After the fermentation, the contents of ergothioneine in the fermentation broths were determined, and the results were shown in Table 41.

The experimental results showed that adjusting the pH of the fermentation broth to 4.8-6.3 on the $4^{th}$ day of fermentation was beneficial to improve the accumulation of ergothioneine in the fermentation broth, among which, when pH was adjusted to 6.0 on the $4^{th}$ day, the content of ergothioneine in the fermentation broth was the highest and reached 136.9 mg/L, which was improved by 17.7% compared with that in the control group.

TABLE 40

Effect of temperature adjustment in the process of fermentation on ergothioneine accumulation by fermentation

| Adjustment time (days) | 0-15 (control group) | 0-12-15 | 0-8-15 | 0-4-15 | 0-4-12-15 | 0-4-8-15 | 0-4-15 |
|---|---|---|---|---|---|---|---|
| Adjustment temperature (° C.) | 25 | 25-28 | 25-28 | 25-28 | 25-28-31 | 25-28-31 | 25-31 |
| Content of ergothioneine in fermentation broth (mg/L) | 115.2 ± 1.56 | 125.9 ± 2.61 | 121.9 ± 1.13 | 131.8 ± 2.94 | 128.7 ± 3.02 | 122.3 ± 1.02 | 136.1 ± 1.18 |

Example 38: pH Adjustment in the Process of Fermentation Improves Ergothioneine Accumulation by Fermentation The fermentation broths were prepared with soybean cake powder of 15 g/L as nitrogen source of the seed medium according to the same method as in Example 1, except for adjusting pH of the fermentation broth to 4.8, 5.0, 5.5, 6.0, and 6.3, respectively on the $4^{th}$ day of fermentation, and the above pH is maintained to the end of fermentation, while the test group without controlling pH in the process of fermentation was used as a control group (wherein, the natural pH was initially 5.4, slowly rose in the process of fermentation, and was about 6.8 at the end of fermentation). *Pleurotus*

TABLE 41

Effect of pH adjustment on the 4$^{th}$ day of fermentation on ergothioneine accumulation by fermentation

| pH adjustment | control group | 4.8 | 5.0 | 5.5 | 6.0 | 6.3 |
|---|---|---|---|---|---|---|
| Content of ergothioneine in fermentation broth (mg/L) | 116.3 ± 3.19 | 123.1 ± 2.26 | 127.8 ± 1.97 | 131.5 ± 2.74 | 136.9 ± 3.54 | 125.9 ± 3.03 |

Example 39: Ergothioneine Accumulation by Fermentation with 75 L Automatic Control Fermentor Seed medium in shake flasks: corn flour 30 g/L, soybean cake powder 15 g/L, α-amylase 80 U/L, KH$_2$PO$_4$ 3 g/L, MgSO$_4$·7H$_2$O 1.5 g/L, and a balance of water, wherein 1 L triangular flask was loaded with a liquid volume of 300 mL, and sterilized at 121° C. for 20 min.

Medium in a 75 L fermentor: glycerol 50 g/L, casein peptone 35 g/L, KH$_2$PO$_4$ 3 g/L, MgSO$_4$·7H$_2$O 1.5 g/L, and a balance of water, wherein the fermentor was loaded with a liquid volume of 45.6 L, and sterilized at 121° C. for 20 min.

A lawn of the strain CGMCC No. 6232 was picked from the PDA slant and inoculated into the seed medium, cultured on a shaker at 150 rpm at 25° C. for 4.5 days, to obtain a seed liquor. The seed liquor was inoculated with an inoculation amount of 6.6% in volume ratio into the fermentor with a fermentor pressure of 0.05 MPa, a culture temperature of 25° C., an initial ventilation rate of 10 L/min, an initial stirring speed of 100 rpm, dissolved oxygen coupling with ventilation rate and stirring speed simultaneously, dissolved oxygen controlled at 30% in the process of fermentation. After fermentation for 14 days, it was determined that the content of extracellular ergothioneine in the filtrate was 24.3 mg/L, and the content of ergothioneine in the fermentation broth was 144.7 mg/L.

Example 40: Addition of Amino Acid in 75 L Automatic Control Fermentor Improves Ergothioneine Accumulation by Fermentation The fermentation of ergothioneine was carried out with 75 L fermentor according to the same method as in Example 39, except that glycerol content was 75 g/L, casein peptone content was 50 g/L in the medium, and 14 mmol/L methionine and 7.5 mmol/L cysteine were additionally added. The dissolved oxygen was controlled at 30% in 0-7 days in the process of fermentation, and at 15% in 8-14 days in the process of fermentation. After fermentation for 14 days, it was determined that the content of extracellular ergothioneine in the filtrate was 56.2 mg/L, and the content of ergothioneine in fermentation broth was 258.2 g/L.

Example 41: Increasing Fermentor Pressure and Dissolved Oxygen in Fermentor Improves Ergothioneine Accumulation by Fermentation The fermentation of ergothioneine was carried out with 75 L fermentor according to the same method as in Example 40, except that the fermentor pressure was 0.1 MPa, and the dissolved oxygen was controlled at 30% in the process of fermentation. After fermentation for 12.5 days, it was determined that the content of extracellular ergothioneine in the filtrate was 61.7 mg/L, and the content of ergothioneine in the fermentation broth was 352.8 mg/L.

Example 42: Addition of EDTA Improves the Content of Extracellular Ergothioneine in the Filtrate The fermentation broths were prepared with soybean cake powder of 15 g/L as nitrogen source of the seed medium according to the same method as in Example 1, except for additionally adding ethylenediaminetetraacetic acid (EDTA) of 0.05 g/L, 0.1 g/L, 0.3 g/L and 0.5 g/L into the fermentation basal mediums, respectively, while the fermentation basal medium without EDTA was used as a control group. Pleurotus ostreatus mycelia CGMCC No. 6232 were subjected to fermentation and culture. After the fermentation, the contents of extracellular ergothioneine in the filtrates were determined, and it was found that addition of EDTA may improve the contents of extracellular ergothioneine, among which, when the added amount was 0.5 g/L, the content of extracellular ergothioneine in the filtrate was the highest and reached 9.28 mg/L, which was improved by 91.3% compared with 4.85 mg/L in the control group.

Example 43: Addition of Isopropyl Alcohol Improves the Content of Extracellular Ergothioneine in the Filtrate The fermentation broths were prepared with soybean cake powder of 15 g/L as nitrogen source of the seed medium according to the same method as in Example 1, except for additionally adding isopropyl alcohol of 0.5% and 2% (V/V) into the fermentation basal mediums, respectively, while the fermentation basal medium without isopropyl alcohol was used as a control group. Pleurotus ostreatus mycelia CGMCC No. 6232 were subjected to fermentation and culture. After the fermentation, the contents of extracellular ergothioneine in the filtrates were determined, and it was found that addition of isopropyl alcohol may improve the contents of extracellular ergothioneine, among which, when the added amount was 2%, the content of extracellular ergothioneine in the filtrate was the highest and reached 10.04 mg/L, which was improved by 178.1% compared with 3.61 mg/L in the control group.

Example 44: Addition of Dimethyl Sulfoxide Improves the Content of Extracellular Ergothioneine in the Filtrate The fermentation broths were prepared with soybean cake powder of 15 g/L as nitrogen source of the seed medium according to the same method as in Example 1, except for additionally adding dimethyl sulfoxide of 0.5% and 2% (V/V) into the fermentation basal mediums, respectively, while the fermentation basal medium without dimethyl sulfoxide was used as a control group. *Pleurotus ostreatus* mycelia CGMCC No. 6232 were subjected to fermentation and culture. After the fermentation, the contents of extracellular ergothioneine in the filtrates were determined, and it was found that addition of isopropyl alcohol may improve the contents of extracellular ergothioneine, among which, when the added amount was 2%, the content of extracellular ergothioneine in the filtrate was the highest and reached 10.18 mg/L, which was improved by 182% compared with 3.61 mg/L in the control group.

It is demonstrated from the above examples that, using soybean cake powder as nitrogen source of the seed medium for fermentation of *Pleurotus ostreatus* CGMCC No. 6232 to synthesize ergothioneine, properly increasing the amount of carbon sources and nitrogen sources in the fermentation medium, adding any one or more compounds mentioned above into the fermentation basal medium, properly adjusting the temperature of fermentation in the process of fermentation, properly adjusting the pH of the fermentation broth in the process of fermentation, and/or properly adjusting the pressure and the dissolved oxygen in the process of fermentation, may significantly improve the fermentation level of ergothioneine. In particular, adding any one or more compounds of tween, Fluconazole, Miconazole, Ketoconazole, ethylenediaminetetraacetic acid (EDTA), isopropyl alcohol and dimethyl sulfoxide into the fermentation basal medium may also improve the content of extracellular ergothioneine in the fermentation broth. The above examples are only illustrative for the examples in which certain of the compounds are added in combination, but it can be understood by one skilled in the art that, other different combinations of the above compounds may also significantly improve the fermentation level of ergothioneine, even with a synergistic effect.

PRACTICAL APPLICABILITY

The present disclosure provides a method for producing ergothioneine, which may significantly improve ergothioneine and obtain a higher yield of ergothioneine, and thus is suitable for practical application.

Although the present disclosure is illustrated herein in detail, the present disclosure is not limited thereto. One skilled in the art may make modifications based on the principles of the present disclosure. Therefore, it should be understood that various modifications based on the principles of the present disclosure are included within the protection scope of the present disclosure.

The invention claimed is:

1. A method for producing ergothioneine, comprising the steps of:
   (a) inoculating *Pleurotus ostreatus* strain CGMCC No.6232 into a seed medium, and culturing it to prepare a seed liquor, wherein the seed medium uses soybean cake powder as nitrogen source; and
   (b) inoculating the seed liquor into a fermentation basal medium, and then culturing it to obtain a fermentation broth of *Pleurotus ostreatus* mycelia, wherein ergothioneine is accumulated in mycelial cells of *Pleurotus ostreatus* mycelia; and
   (c) extracting ergothioneine from the mycelial cells;
wherein using soybean cake powder as the nitrogen source in step (a) results in an increased amount of the production of ergothioneine in mycelial cells of said *Pleurotus ostreatus* strain CGMCC No.6232 in step (b) as compared to using soybean meal powder with the same concentration as nitrogen source of the seed medium.

2. The method according to claim 1, wherein the culturing process in step (a) is carried out at 19-31° C. for at least 3 days, the culturing process in step (b) is carried out at 19-31° C. for at least 6 days, and the inoculation amount in step (b) is 4-20% (V/V).

3. The method according to claim 1, wherein the seed medium comprises 15-50 g/L corn flour, 5-35 g/L soybean cake powder, 20-80 U/L α-amylase, 1-6 g/L $KH_2PO_4$, 0.2-5 g/L $MgSO_4 \cdot 7H_2O$, and a balance of water.

4. The method according to claim 3, wherein the content of the soybean cake powder is 15-35 g/L.

5. The method according to claim 1, wherein the fermentation basal medium comprises 10-95 g/L glycerol, 10-80 g/L casein peptone, 2-4 g/L $KH_2PO_4$, 0.5-2 g/L $MgSO_4 \cdot 7H_2O$, and a balance of water.

6. The method according to claim 5, wherein the fermentation basal medium comprises 65-95 g/L glycerol.

7. The method according to claim 5, wherein the fermentation basal medium comprises 40-80 g/L casein peptone.

8. The method according to claim 1, wherein at least one member selected from the group consisting of $NH_4Cl$, $NH_4NO_3$, NaCl, polyethylene glycol, folic acid, vitamin B1 (VB1), indolebutyric acid, citric acid, pyruvic acid, arginine, lysine, leucine, aspartic acid, glutamic acid, betaine, histidine, cysteine, methionine, tween, span, chitosan, Fluconazole, Miconazole, Ketoconazole, ethylenediaminetetraacetic acid (EDTA), isopropyl alcohol and dimethyl sulfoxide is added into the fermentation basal medium.

9. The method according to claim 8, wherein said at least one member is selected from the group consisting of tween, Fluconazole, Miconazole, Ketoconazole, ethylenediaminetetraacetic acid (EDTA), isopropyl alcohol and dimethyl sulfoxide.

10. The method according to claim 1, wherein at least one member selected from the group consisting of $NH_4Cl$ 0.5 g/L-12 g/L, $NH_4NO_3$ 0.5 g/L-10 g/L, NaCl 0.5 g/L-20 g/L, polyethylene glycol 0.2 g/L-5 g/L, folic acid 0.08 g/L-2.56 g/L, VB1 0.01 g/L-0.8 g/L, indolebutyric acid 0.1 mg/L-4 mg/L, citric acid 0.01 g/L-0.8 g/L, pyruvic acid 0.05 g/L-4.5 g/L, arginine 0.1 g/L-7 g/L, lysine 0.1 g/L-8 g/L, leucine 0.02 g/L-0.5 g/L, aspartic acid 0.05 g/L-9 g/L, glutamic acid 1 µmol/L-100 µmol/L, betaine 50 mmol/L-250 mmol/L, histidine 0.1 mmol/L-3 mmol/L, cysteine 2 mmol/L-45 mmol/L, methionine 3 mmol/L-45 mmol/L, tween 0.5 g/L-50 g/L, span 0.2 g/L-10 g/L, chitosan 0.2 g/L-0.4 g/L, Fluconazole 2 mg/L-80 mg/L, Miconazole 0.5 mg/L-50 mg/L, Ketoconazole 0.5 mg/L-50 mg/L, ethylenediaminetetraacetic acid (EDTA) 0.05 g/L-0.5 g/L, isopropyl alcohol 0.5%-2% (V/V) and dimethyl sulfoxide 0.5%-2% (V/V) in specified amounts is added into the fermentation basal medium.

11. The method according to claim 1, wherein the temperature of fermentation is adjusted to 25-31° C. in the process of fermentation in step (b).

12. The method according to claim 1, wherein the pH of the fermentation broth is adjusted to 4.8-6.3 in the process of fermentation in step (b).

13. The method according to claim 1, wherein the pressure is adjusted to 0.05-0.1 Mpa and the dissolved oxygen is adjusted to 15-30% in the process of fermentation in step (b).

14. The method according to claim 1, comprising the steps of:
   (a) inoculating *Pleurotus ostreatus* strain CGMCC No.6232 into a seed medium, and culturing it at 25-28° C. for 3-5 days to prepare a seed liquor, wherein the seed medium comprises 25-40 g/L corn flour, 15-35 g/L soybean cake powder, 30-80 U/L α-amylase, 2-4.5 g/L KH$_2$PO$_4$, 0.2-3 g/L MgSO$_4$.7H$_2$O, and a balance of water; and (b) inoculating the seed liquor into a fermentation basal medium with an inoculation amount of 4-20% (V/V), and culturing it at 25-31° C. for at least 6 days to obtain a fermentation broth of *Pleurotus ostreatus* mycelia, wherein the fermentation basal medium comprises 65-95 g/L glycerol, 40-80 g/L casein peptone, 2-4 g/L KH$_2$PO$_4$, 0.5-2 g/L MgSO$_4$.7H$_2$O, 7.5-15 mmol/L methionine, 7.5-15 mmol/L cysteine, and a balance of water, wherein ergothioneine is accumulated in mycelial cells of *Pleurotus ostreatus* mycelia; and (c) extracting ergothioneine from the mycelial cells; wherein using soybean cake powder as the nitrogen source in step (a) results in an increased amount of the production of ergothioneine in mycelial cells of said *Pleurotus ostreatus* strain CGMCC No.6232 in step (b) as compared to using soybean meal powder with the same concentration as nitrogen source of the seed medium.

15. The method according to claim 1, comprising the steps of:

(a) inoculating *Pleurotus ostreatus* strain CGMCC No.6232 into a seed medium, and culturing it at 25° C. for 4 days to prepare a seed liquor, wherein the seed medium comprises 30 g/L corn flour, 15 g/L soybean cake powder, 80 U/L α-amylase, 3 g/L KH$_2$PO$_4$, 1.5 g/L MgSO$_4$.7H$_2$O, and a balance of water; and (b) inoculating the seed liquor into a fermentation basal medium with an inoculation amount of 5% (V/V) and culturing it at 25° C. for 3 days, and then adjusting the pH to 6.0 and culturing it at 31° C. for 12 days to obtain a fermentation broth of *Pleurotus ostreatus* mycelia, wherein the fermentation basal medium comprises 75 g/L glycerol, 50 g/L casein peptone, 3 g/L KH$_2$PO$_4$, 1.5 g/L MgSO$_4$.7H$_2$O, 14 mmol/L methionine, 7.5 mmol/L cysteine, and a balance of water, wherein ergothioneine is accumulated in mycelial cells of *Pleurotus ostreatus* mycelia; and (c) extracting ergothioneine from the mycelial cells; wherein using soybean cake powder as the nitrogen source in step (a) results in an increased amount of the production of ergothioneine in mycelial cells of said *Pleurotus ostreatus* strain CGMCC No.6232 in step (b) as compared to using soybean meal powder with the same concentration as nitrogen source of the seed medium.

* * * * *